US012387332B2

(12) United States Patent
Nakayama et al.

(10) Patent No.: US 12,387,332 B2
(45) Date of Patent: Aug. 12, 2025

(54) INFORMATION PROCESSING DEVICE, RADIOGRAPHY APPARATUS, INFORMATION PROCESSING METHOD, AND INFORMATION PROCESSING PROGRAM

(71) Applicant: FUJIFILM CORPORATION, Tokyo (JP)

(72) Inventors: Hiroki Nakayama, Kanagawa (JP); Yoshinari Oda, Kanagawa (JP); Lisako Nobuyama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 460 days.

(21) Appl. No.: 17/930,720

(22) Filed: Sep. 9, 2022

(65) Prior Publication Data

US 2023/0005149 A1    Jan. 5, 2023

Related U.S. Application Data

(63) Continuation of application No. PCT/JP2021/011505, filed on Mar. 19, 2021.

(30) Foreign Application Priority Data

Mar. 31, 2020  (JP) ................................. 2020-065268
Dec. 28, 2020  (JP) ................................. 2020-219603

(51) Int. Cl.
*G06T 7/00*   (2017.01)
*A61B 6/00*   (2024.01)
(Continued)

(52) U.S. Cl.
CPC .......... *G06T 7/0014* (2013.01); *A61B 6/0414* (2013.01); *A61B 6/4417* (2013.01);
(Continued)

(58) Field of Classification Search
CPC .......... G06T 7/0014; G06T 7/13; G06T 7/90; G06T 2207/10024; G06T 2207/10028;
(Continued)

(56) References Cited

U.S. PATENT DOCUMENTS 6,647,089 B1 * 11/2003 Virta ...................... A61B 6/502
                                                             378/37
2009/0310749 A1   12/2009 Kojima
(Continued)

FOREIGN PATENT DOCUMENTS

DE    102018211106 A1    1/2020
JP    2009-297273 A     12/2009
(Continued)

OTHER PUBLICATIONS

English language translation of the following: Office action dated Nov. 7, 2023 from the JPO in a Japanese patent application No. 2022-511929 corresponding to the instant patent application. This office action translation is submitted now in order to supplement the understanding of the cited references which are being disclosed in the instant Information Disclosure Statement.
(Continued)

*Primary Examiner* — Nay A Maung
*Assistant Examiner* — Dustin Bilodeau
(74) *Attorney, Agent, or Firm* — SOLARIS Intellectual Property Group, PLLC

(57) ABSTRACT

A CPU acquires a distance image or a visible light image captured by a TOF camera or a visible light camera that has, as an imageable region, a region including an irradiation region which is a space in which a breast of a subject imaged by a mammography apparatus is irradiated with radiation emitted from a radiation source and detects whether or not
(Continued)

a foreign object other than an object to be imaged is present in the irradiation region on the basis of the distance image or the visible light image.

27 Claims, 23 Drawing Sheets

(51) Int. Cl.
| | | |
|---|---|---|
| A61B 6/04 | (2006.01) | |
| A61B 6/50 | (2024.01) | |
| G06T 7/13 | (2017.01) | |
| G06T 7/90 | (2017.01) | |
| G06V 10/22 | (2022.01) | |

(52) U.S. Cl.
CPC .............. *A61B 6/502* (2013.01); *A61B 6/542* (2013.01); *G06T 7/13* (2017.01); *G06T 7/90* (2017.01); *G06V 10/22* (2022.01); *G06T 2207/10024* (2013.01); *G06T 2207/10028* (2013.01); *G06T 2207/10064* (2013.01); *G06T 2207/10116* (2013.01); *G06T 2207/30068* (2013.01); *G06T 2207/30196* (2013.01); *G06T 2207/30204* (2013.01); *G06V 2201/03* (2022.01)

(58) Field of Classification Search
CPC . G06T 2207/10064; G06T 2207/10116; G06T 2207/30068; G06T 2207/30196; G06T 2207/30204; G06T 2207/10121; G06T 2207/30168; A61B 6/0414; A61B 6/4417; A61B 6/502; A61B 6/542; A61B 6/08; A61B 6/10; A61B 6/107; G06V 10/22; G06V 2201/03

See application file for complete search history.

(56) References Cited

U.S. PATENT DOCUMENTS

| | | | |
|---|---|---|---|
| 2013/0281818 A1* | 10/2013 | Vija | A61B 5/704 600/407 |
| 2013/0342851 A1 | 12/2013 | Dresel et al. | |
| 2017/0071558 A1 | 3/2017 | Hoornaert et al. | |
| 2017/0265828 A1* | 9/2017 | Tsujii | A61B 5/0091 |
| 2018/0140270 A1 | 5/2018 | Profio et al. | |
| 2018/0271467 A1 | 9/2018 | Nishi | |
| 2018/0303440 A1* | 10/2018 | Sung | A61B 6/4035 |
| 2019/0021677 A1 | 1/2019 | Grbic et al. | |
| 2019/0049604 A1 | 2/2019 | Pickert et al. | |
| 2019/0209106 A1* | 7/2019 | Bechtold | A61B 6/54 |
| 2021/0307711 A1* | 10/2021 | Vancamberg | A61B 6/465 |

FOREIGN PATENT DOCUMENTS

| | | | |
|---|---|---|---|
| JP | 2011-104149 A | 6/2011 | |
| JP | 2014-138667 A | 7/2014 | |
| JP | 2017-506965 A | 3/2017 | |
| JP | 2017-164312 A | 9/2017 | |
| JP | 2018-157941 A | 10/2018 | |
| JP | 2019-000460 A | 1/2019 | |
| JP | 2019-536546 A | 12/2019 | |
| JP | 7597140 B2 * | 12/2024 | ............. A61B 6/488 |

OTHER PUBLICATIONS

Extended European Search Report dated Aug. 24, 2023, issued in corresponding EP Patent Application No. 21779051.8.
International Search Report issued in International Application No. PCT/JP2021/011505 on Jun. 1, 2021.
Written Opinion of the ISA issued in International Application No. PCT/JP2021/011505 on Jun. 1, 2021.

* cited by examiner

FOREIGN OBJECT TENDS TO ENTER RIGHT SIDE OF CHEST WALL

INFORMATION PROCESSING DEVICE, RADIOGRAPHY APPARATUS, INFORMATION PROCESSING METHOD, AND INFORMATION PROCESSING PROGRAM

CROSS-REFERENCE TO RELATED APPLICATIONS

This application is a continuation application of International Application No. PCT/JP2021/011505, filed on Mar. 19, 2021, the disclosure of which is incorporated herein by reference in its entirety. Further, this application claims priority from Japanese Patent Application No. 2020-065268, filed on Mar. 31, 2020, and Japanese Patent Application No. 2020-219603, filed on Dec. 28, 2020, the disclosures of which are incorporated herein by reference in their entireties.

BACKGROUND

1. Technical Field

The present disclosure relates to an information processing device, a radiography apparatus, an information processing method, and an information processing program.

2. Description of the Related Art

In capture of a radiographic image by a radiography apparatus, in a case in which a radiographic image is captured in a state in which a foreign object, such as a part other than an object to be imaged in a subject, enters an irradiation region of radiation emitted from a radiation source, it may be necessary to re-capture a radiographic image. Therefore, in the capture of the radiographic image, a user checks an irradiation range of the radiation indicated by visible light to check whether or not a foreign object is present in the irradiation region of the radiation. For example, JP2018-157941A discloses a technique that indicates an irradiation field of radiation with visible light.

SUMMARY

As described above, the foreign object that has entered the irradiation region of the radiation is detected in the related art. However, in the technique according to the related art, in some cases, it is not sufficient to detect the foreign object that has entered the irradiation region of the radiation. For example, in some cases, after the user checks positioning, the subject moves, and a part of the subject other than the object to be imaged enters the irradiation region. The technique according to the related art is not capable of responding to this case, and re-imaging may be required.

The present disclosure has been made in consideration of the above circumstances, and an object of the present disclosure is to provide an information processing device, a radiography apparatus, an information processing method, and an information processing program that can appropriately detect whether or not a foreign object other than an object to be imaged is present in an irradiation region of radiation.

According to a first aspect of the present disclosure, there is provided an information processing device comprising: at least one processor; and a memory that stores commands executable by the processor. The processor acquires a captured image captured by an imaging device that has, as an imageable region, a region including an irradiation region which is a space in which an object to be imaged by a radiography apparatus is irradiated with radiation emitted from a radiation source and detects whether or not a foreign object other than the object to be imaged is present in the irradiation region on the basis of the captured image.

According to a second aspect of the present disclosure, in the information processing device according to the first aspect, the processor may acquire information indicating the irradiation region and detect whether or not the foreign object is present in the irradiation region indicated by the information.

According to a third aspect of the present disclosure, in the information processing device according to the first aspect or the second aspect, the processor may derive a space between the object to be imaged and the radiation source in the irradiation region as a detection region and detect whether or not the foreign object is present in the derived detection region.

According to a fourth aspect of the present disclosure, in the information processing device according to the third aspect, the radiography apparatus may be a mammography apparatus that captures a radiographic image of a breast of a subject, and the detection region may be a space between a compression member that compresses the breast and the radiation source in the irradiation region.

According to a fifth aspect of the present disclosure, in the information processing device according to the third aspect or the fourth aspect, the imaging device may be a distance image capture device that captures a distance image indicating a distance to the object to be imaged as the captured image.

According to a sixth aspect of the present disclosure, in the information processing device according to the fifth aspect, the processor may detect whether or not the foreign object is present in the detection region using an image corresponding to the detection region in the distance image.

According to a seventh aspect of the present disclosure, in the information processing device according to the sixth aspect, the processor may detect whether or not the foreign object is present in the detection region on the basis of a distance between the imaging device and each position in the detection region derived on the basis of a position of the detection region and a distance between the imaging device and the object to be imaged indicated by the image corresponding to the detection region in the distance image.

According to an eighth aspect of the present disclosure, in the information processing device according to any one of the fifth to seventh aspects, the distance image capture device may capture the distance image using a time-of-flight (TOF) method.

According to a ninth aspect of the present disclosure, in the information processing device according to any one of the first to fourth aspects, the imaging device may be a visible light image capture device that captures a visible light image of the object to be imaged as the captured image.

According to a tenth aspect of the present disclosure, in the information processing device according to the first aspect, the radiography apparatus may be a mammography apparatus that captures a radiographic image of a breast compressed by a compression member, and the imaging device may be a visible light image capture device that captures a visible light image of the object to be imaged as the captured image. The processor may detect whether or not the foreign object is present on the basis of a chipping of an image of the compression member in the captured image.

According to an eleventh aspect of the present disclosure, in the information processing device according to the tenth aspect, the processor may detect whether or not the foreign object is present on the basis of a chipping of a subject on the breast in the image of the compression member.

According to a twelfth aspect of the present disclosure, in the information processing device according to the tenth aspect or the eleventh aspect, the processor may use an image of an edge portion of the compression member as the image of the compression member.

According to a thirteenth aspect of the present disclosure, in the information processing device according to the twelfth aspect, the processor may acquire compression member information indicating a type of the compression member and estimate at least one of a position or a size of the image of the edge portion included in the captured image on the basis of the compression member information.

According to a fourteenth aspect of the present disclosure, in the information processing device according to the twelfth aspect or the thirteenth aspect, the edge portion of the compression member may have a color different from a color of at least one of a compression surface, which compresses the breast, in the compression member or an imaging table on which the breast is placed, and the processor may extract the image of the edge portion of the compression member from the captured image on the basis of the color of the edge portion.

According to a fifteenth aspect of the present disclosure, in the information processing device according to the twelfth aspect or the thirteenth aspect, the edge portion of the compression member may be processed to be distinguishable from an image of a compression surface, which compresses the breast, in the compression member in the captured image, and the processor may extract the image of the edge portion from the captured image.

According to a sixteenth aspect of the present disclosure, in the information processing device according to the fifteenth aspect, the edge portion of the compression member may be highlighted by at least one of a phosphorescent material or a fluorescent material.

According to a seventeenth aspect of the present disclosure, in the information processing device according to any one of the tenth to sixteenth aspects, the processor may detect whether or not the foreign object is present on the basis of a chipping of an image of a region corresponding to a type of the imaging in an image of the compression member.

According to an eighteenth aspect of the present disclosure, in the information processing device according to the first aspect, the radiography apparatus may be a mammography apparatus that captures a radiographic image of a breast compressed by a compression member, and the imaging device may be a visible light image capture device that captures, as the captured image, a visible light image obtained by capturing a projection image projected onto an irradiation surface of the compression member, which is irradiated with the radiation, by an image projection device.

According to a nineteenth aspect of the present disclosure, in the information processing device according to the eighteenth aspect, the projection image projected onto the irradiation surface may be projected within a range of an irradiation field of the radiation.

According to a twentieth aspect of the present disclosure, in the information processing device according to the eighteenth aspect or the nineteenth aspect, the projection image projected onto the irradiation surface may be projected within a range of an irradiation field of the radiation in a state in which visible light is not emitted by an irradiation field projection device that projects the range of the irradiation field of the radiation with the visible light.

According to a twenty-first aspect of the present disclosure, in the information processing device according to any one of the eighteenth to twentieth aspects, the processor may detect whether or not the foreign object is present on the basis of an image of a region corresponding to an inside of an irradiation field of the radiation in the captured image.

According to a twenty-second aspect of the present disclosure, in the information processing device according to any one of the eighteenth to twenty-first aspects, the processor may detect whether or not the foreign object is present on the basis of a comparison result between the projection image and the captured image.

According to a twenty-third aspect of the present disclosure, in the information processing device according to any one of the eighteenth to twenty-first aspects, the processor may control the image projection device such that the projection image is projected onto a region including an irradiation field of the radiation.

According to a twenty-fourth aspect of the present disclosure, in the information processing device according to the twenty-third aspect, the processor may derive a size and position of the irradiation field on the irradiation surface of the compression member according to a height of the compression member and perform control to project the projection image according to the derived size and position of the irradiation field.

According to a twenty-fifth aspect of the present disclosure, in the information processing device according to the first aspect, the radiography apparatus may be a mammography apparatus that captures a radiographic image of a breast compressed by a compression member, and the imaging device may be a visible light image capture device that captures, as the captured image, an image of a state in which a range of an irradiation field of the radiation is projected onto the compression member by an irradiation field projection device that projects the range of the irradiation field of the radiation with visible light.

According to a twenty-sixth aspect of the present disclosure, in the information processing device according to any one of the first to twenty-fifth aspects, in a case in which it is detected that the foreign object is present, the processor may prohibit the emission of the radiation by the radiation source.

According to a twenty-seventh aspect of the present disclosure, in the information processing device according to any one of the first to twenty-sixth aspects, in a case in which it is detected that the foreign object is present, the processor may output a warning related to the foreign object.

According to a twenty-eighth aspect of the present disclosure, in the information processing device according to any one of the first to twenty-seventh aspects, a plurality of the imaging devices may be provided, and an imageable region of all of the plurality of imaging devices, which is a combination of the imageable regions of each of the plurality of imaging devices, may include the irradiation region.

According to a twenty-ninth aspect of the present disclosure, there is provided a radiography apparatus comprising: the information processing device according to the present disclosure; and an imaging device.

Further, in order to achieve the above object, according to a thirtieth aspect of the present disclosure, there is provided an information processing method executed by a computer. The information processing method comprises: acquiring a captured image captured by an imaging device that has, as an imageable region, a region including an irradiation region which is a space in which an object to be imaged by a radiography apparatus is irradiated with radiation emitted from a radiation source; and detecting whether or not a foreign object other than the object to be imaged is present in the irradiation region on the basis of the captured image.

According to a thirty-first aspect of the present disclosure, there is provided an information processing program that causes a computer to execute a process comprising: acquiring a captured image captured by an imaging device that has, as an imageable region, a region including an irradiation region which is a space in which an object to be imaged by a radiography apparatus is irradiated with radiation emitted from a radiation source; and detecting whether or not a foreign object other than the object to be imaged is present in the irradiation region on the basis of the captured image.

According to the present disclosure, it is possible to appropriately detect whether or not a foreign object other than an object to be imaged is present in an irradiation region of radiation.

BRIEF DESCRIPTION OF THE DRAWINGS

Exemplary embodiments according to the technique of the present disclosure will be described in detail based on the following figures, wherein.

DESCRIPTION OF THE PREFERRED EMBODIMENTS

Hereinafter, embodiments of the invention will be described in detail with reference to the drawings. In addition, each of the embodiments does not limit the invention.

First Embodiment

Figure 1:
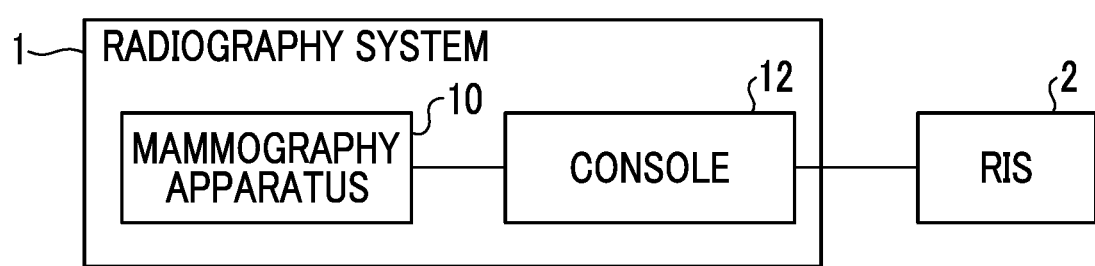
FIG. 1 is a schematic diagram illustrating an example of an overall configuration of a radiography system according to a first embodiment.

First, an example of an overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of an information processing device according to the present disclosure.

Figure 2:
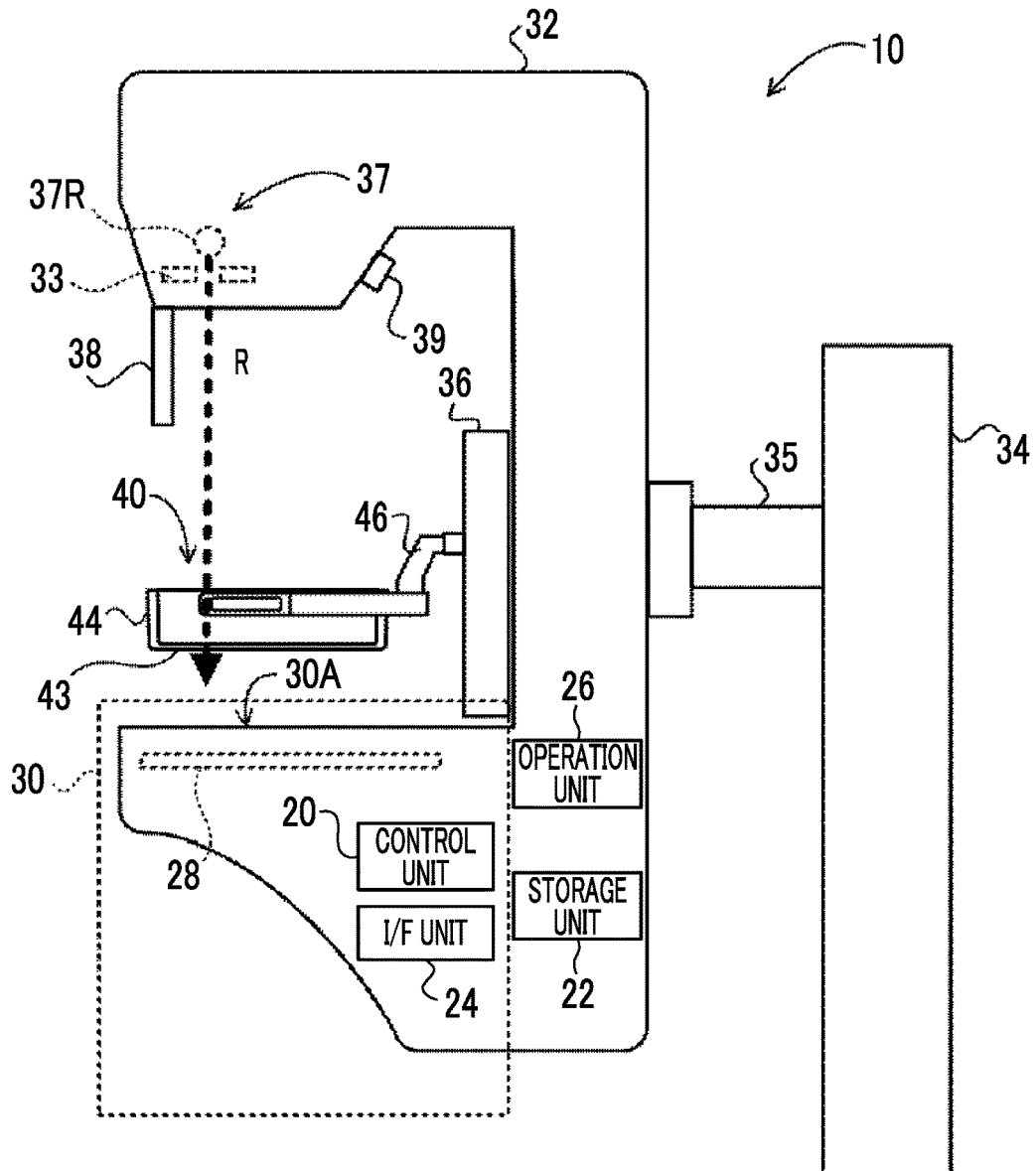
FIG. 2 is a side view illustrating an example of the outward appearance of a mammography apparatus according to the first embodiment.

First, the mammography apparatus 10 according to this embodiment will be described. FIG. 2 is a side view illustrating an example of the outward appearance of the mammography apparatus 10 according to this embodiment. In addition, FIG. 2 illustrates an example of the outward appearance of the mammography apparatus 10 as viewed from the right side of a subject.

The mammography apparatus 10 according to this embodiment irradiates a breast of the subject as an object with radiation R (for example, X-rays) to capture a radiographic image of the breast. In addition, the mammography apparatus 10 may be an apparatus that images the breast of the subject not only in a state in which the subject is standing up (standing state) but also in a state in which the subject is sitting on, for example, a chair (including a wheelchair) (sitting state).

As illustrated in FIG. 2, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, an operation unit 26 is provided as a plurality of switches in, for example, the imaging table 30 of the mammography apparatus 10. Further, the operation unit 26 may be provided as a touch panel switch or may be provided as a foot switch that is operated by the user's feet.

The radiation detector 28 detects the radiation R transmitted through the breast which is the object. As illustrated in FIG. 2, the radiation detector 28 is disposed in the imaging table 30. In the mammography apparatus 10 according to this embodiment, in a case in which imaging is performed, the breast of the subject is positioned on an imaging surface 30A of the imaging table 30 by a user such as a doctor or a radiology technician.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

Figure 3:
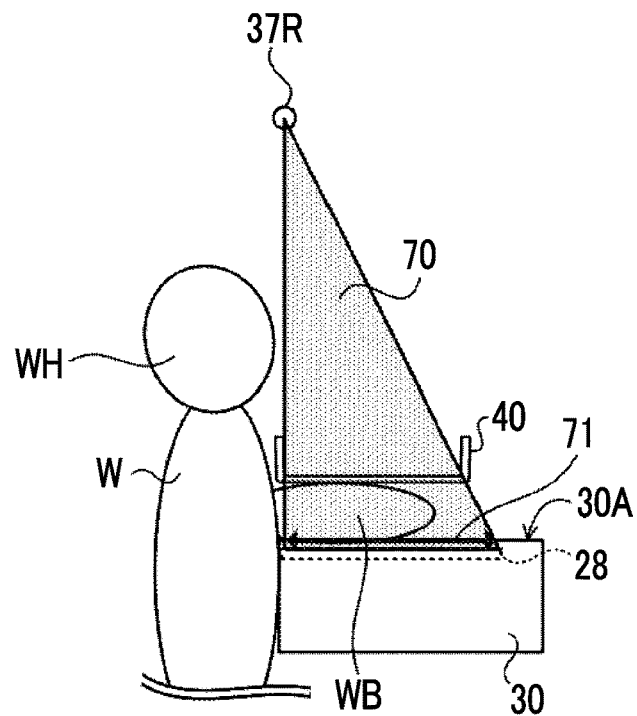
FIG. 3 is a diagram illustrating an irradiation region of radiation.

A radiation emitting unit 37 comprises a radiation source 37R having a radiation tube (not illustrated) that emits the radiation R to the imaging table 30. Further, the radiation emitting unit 37 comprises a collimator 33. The control unit 20 controls the collimator 33 such that an irradiation region 70 of the radiation R is set as illustrated in FIG. 3 and an irradiation field 71 of the radiation R on the imaging surface 30A of the imaging table 30 is defined. FIG. 3 illustrates an example of the irradiation region 70 of the radiation R emitted from the radiation source 37R in a state in which a breast WB of a subject W imaged by the mammography apparatus 10 is compressed by a compression plate 40. The irradiation region 70 is a space in which an object to be imaged by the mammography apparatus 10 is irradiated with the radiation R emitted from the radiation source 37R. In addition, the size and shape of the irradiation field 71 according to this embodiment are determined according to, for example, the size of an detection surface (not illustrated) of the radiation detector 28 or the size of the breast WB as the object to be imaged. The control unit 20 controls the collimator 33 according to the size and shape of the irradiation field 71. For example, in this embodiment, the irradiation field 71 has a rectangular shape. Therefore, the irradiation region 70 according to this embodiment is a region having a rectangular pyramid shape which has a focus of the radiation tube (not illustrated) of the radiation source 37R as the apex and the irradiation field 71 as the base.

In addition, in this embodiment, the object to be imaged is the breast WB of the subject. However, the object to be imaged is not limited to the breast WB and includes objects, such as markers, whose images are approved to be included in a radiographic image. Further, in this embodiment, for example, the compression plate 40 which is approved to be disposed in the imaging region of the radiographic image in the capture of the radiographic image is also regarded as the object to be imaged. Furthermore, an object which is other than the object to be imaged and enters the irradiation region 70 is referred to as a "foreign object". Examples of the foreign object include the head WH and hands (not illustrated) of the subject W and objects other than the subject W.

As illustrated in FIG. 2, the radiation emitting unit 37 is provided in an arm portion 32 together with the imaging table 30 and a compression unit 36. As illustrated in FIG. 2, a face guard 38 for protecting the subject from the radiation R emitted from the radiation source 37R is attachably and detachably attached at a position of the arm portion 32 near the subject below the radiation emitting unit 37.

Figure 4:
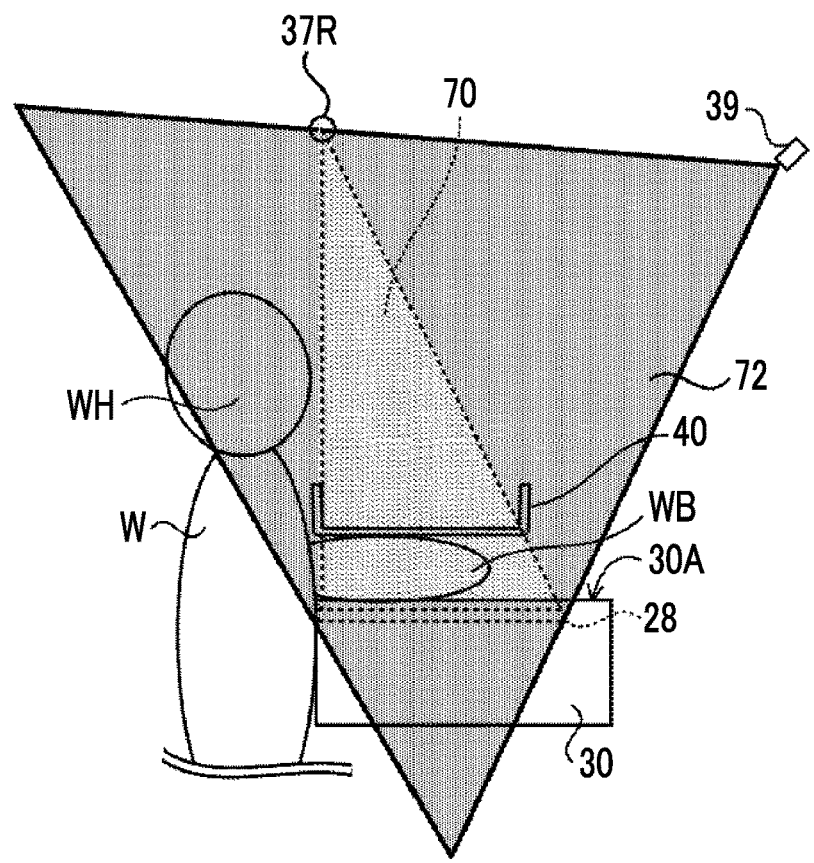
FIG. 4 is a diagram illustrating an imageable region of a TOF camera.

In addition, a time-of-flight (TOF) camera 39 is provided at a position of the arm portion 32 which is away from the subject below the radiation emitting unit 37. The TOF camera 39 is a camera that captures a distance image indicating a distance to the object to be imaged using a TOF method. The TOF camera 39 according to this embodiment is an example of an imaging device and a distance image capture device according to the present disclosure. Specifically, the TOF camera 39 emits light, such as infrared rays, to the object to be imaged and measures the distance between the TOF camera 39 and the object to be imaged on the basis of the time until reflected light is received or a phase change between the emitted light and the received light. In the distance image captured by the TOF camera 39, each pixel has distance information indicating the distance between the TOF camera 39 and the object to be imaged. Further, the distance image means an image from which the distance to the object to be imaged can be derived. Furthermore, as illustrated in FIG. 4, the TOF camera 39 according to this embodiment is disposed in a state in which the entire irradiation region 70 is included in an imageable region 72. Therefore, the distance image captured by the TOF camera 39 includes an image corresponding to the irradiation region 70. In addition, in the TOF camera 39 according to this embodiment, the imageable region 72 is defined by the design.

Further, as illustrated in FIG. 2, the mammography apparatus 10 according to this embodiment comprises the arm portion 32, a base 34, and a shaft portion 35. The arm portion 32 is held by the base 34 to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

Each of the arm portion 32 and the compression unit 36 can be relatively rotated with respect to the base 34, using the shaft portion 35 as a rotation axis. In this embodiment, gears (not illustrated) are provided in each of the shaft portion 35, the arm portion 32, and the compression unit 36. Each gear is switched between an engaged state and a disengaged state to connect each of the arm portion 32 and the compression unit 36 to the shaft portion 35. One or both of the arm portion 32 and the compression unit 36 connected to the shaft portion 35 are rotated integrally with the shaft portion 35.

The compression unit 36 is provided with a compression plate driving unit (not illustrated) that moves a compression plate 40 in the up-down direction (Z-axis direction). The compression plate 40 according to this embodiment has a function of compressing the breast of the subject. A support portion 46 of the compression plate 40 is attachably and detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

As illustrated in FIG. 2, the compression plate 40 according to this embodiment includes a bottom portion 43, a wall portion 44, and the support portion 46 and has a recessed shape in a cross-sectional view in which the bottom portion 43 that comes into contact with the breast of the subject is surrounded by the wall portion 44.

In addition, there are a plurality of types of compression plates 40 that can be attached to the mammography apparatus 10. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only a region in which a lesion is present. Further, other types of compression plates 40 include, for example, a compression plate corresponding to the size of the breast, a compression plate for axillary imaging, and a compression plate for magnification imaging. Furthermore, although the compression plate 40 is referred to as a "compression plate" for convenience, it is not limited to a compression plate using a plate-shaped member. For example, the compression plate 40 may be a compression plate using a film-shaped member.

Meanwhile, the console 12 according to this embodiment has a function of controlling the mammography apparatus 10 using, for example, an imaging order and various kinds of information acquired from a radiology information system (RIS) 2 or the like through a wireless communication local area network (LAN) or the like and instructions input by the user through an operation unit 56 or the like.

Figure 5:
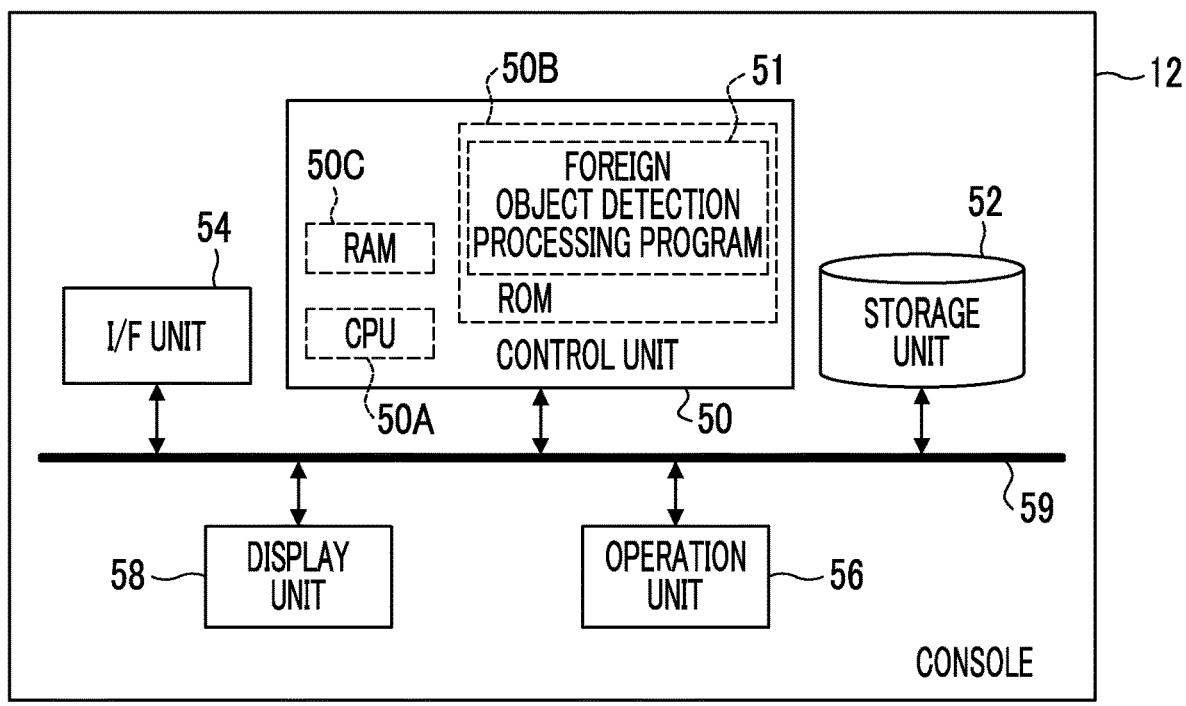
FIG. 5 is a block diagram illustrating an example of a configuration of a console according to the first embodiment.

For example, the console 12 according to this embodiment is a server computer. As illustrated in FIG. 5, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a foreign object detection processing program 51 executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure. Further, the foreign object detection processing program 51 according to this embodiment is an example of an information processing program according to the present disclosure.

For example, the image data of the radiographic image captured by the mammography apparatus 10 and various other kinds of information are stored in the storage unit 52. An HDD or an SSD is given as a specific example of the storage unit 52.

The operation unit 56 is used by the user to input, for example, instructions which are related to the capture of a radiographic image or the like and include an instruction to emit the radiation R, various kinds of information, or the like. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 6:
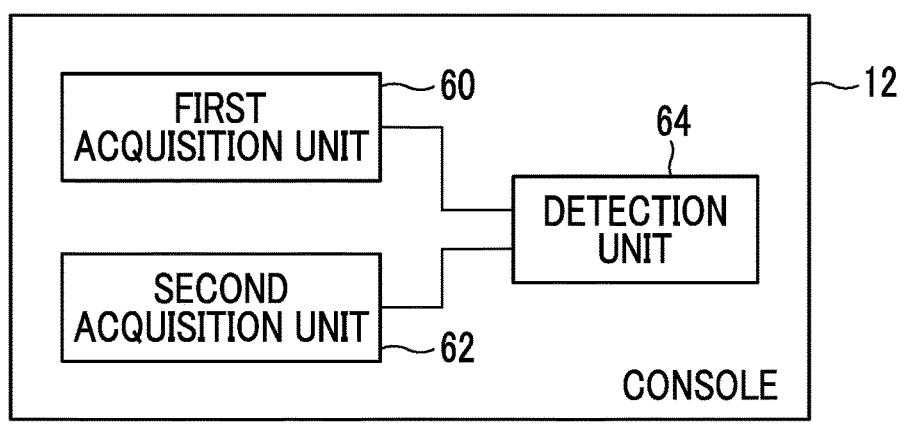
FIG. 6 is a functional block diagram illustrating an example of a functional configuration of the console according to the first embodiment.

In addition, FIG. 6 is a functional block diagram illustrating an example of the functional configuration of the console 12 according to this embodiment. As illustrated in FIG. 6, the console 12 comprises a first acquisition unit 60, a second acquisition unit 62, and a detection unit 64. For example, in the console 12 according to this embodiment, the CPU 50A of the control unit 50 executes the foreign object detection processing program 51 stored in the ROM 50B to function as the first acquisition unit 60, the second acquisition unit 62, and the detection unit 64.

The first acquisition unit 60 has a function of acquiring information indicating the irradiation region 70. In addition, the method by which the first acquisition unit 60 acquires the information indicating the irradiation region 70 is not limited. The irradiation region 70 is determined according to the setting of the collimator 33 and the distance between the radiation source 37R and the imaging surface 30A of the imaging table 30. The setting of the collimator 33 and the distance between the radiation source 37R and the imaging surface 30A can be checked by the mammography apparatus 10. Therefore, for example, first, the control unit 20 of the mammography apparatus 10 derives the irradiation region 70 on the basis of the setting of the collimator 33 and the distance between the radiation source 37R and the imaging surface 30A. Then, the first acquisition unit 60 may acquire the information indicating the irradiation region 70 derived by the control unit 20 from the mammography apparatus 10. Further, the present disclosure is not limited to this embodiment. For example, the console 12 may acquire information indicating the setting of the collimator 33 and information indicating the distance between the radiation source 37R and the imaging surface 30A. Then, the console 12 may derive the information indicating the irradiation region 70 using the acquired information. The first acquisition unit 60 may acquire the derived information indicating the irradiation region 70. The information indicating the irradiation region 70 acquired by the first acquisition unit 60 is output to the detection unit 64.

The second acquisition unit 62 has a function of acquiring the distance image captured by the TOF camera 39. For example, the second acquisition unit 62 according to this embodiment acquires image data indicating the distance image captured by the TOF camera 39 from the TOF camera 39 through the I/F unit 24 and the I/F unit 54. The distance image acquired by the second acquisition unit 62 is output to the detection unit 64.

Figure 7A:
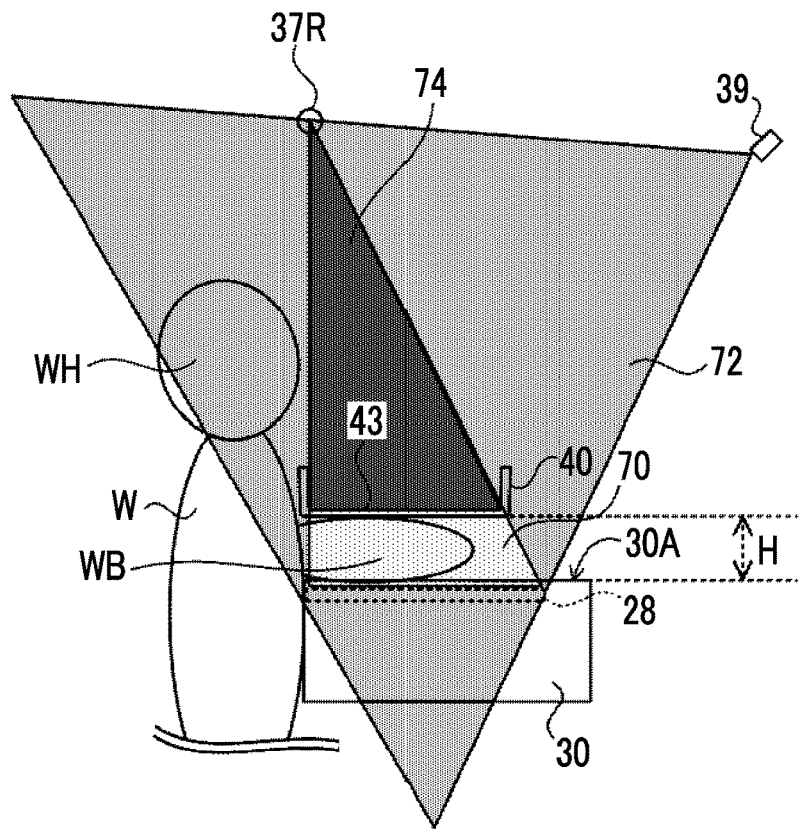
FIG. 7A is a diagram illustrating a detection region.

The detection unit 64 has a function of detecting whether or not a foreign object other than the object to be imaged is present in the irradiation region 70 on the basis of the distance image. For example, as illustrated in FIG. 7A, the detection unit 64 according to this embodiment derives a space between the object to be imaged and the radiation source 37R as a detection region 74 in the irradiation region 70 and detects whether or not a foreign object is present in the derived detection region 74. As illustrated in FIG. 7A, specifically, the detection region 74 according to this embodiment is a space from an upper surface (a surface facing the radiation source 37R) of the bottom portion 43 of the compression plate 40 to the radiation source 37R in the irradiation region 70. More specifically, the detection region 74 is a space from the upper surface of the bottom portion 43 of the compression plate 40 that compresses the breast WB to the radiation source 37R in the irradiation region 70. Therefore, the detection region 74 is determined according to a height H of the breast WB compressed by the compression plate 40, a thickness of the bottom portion 43 of the compression plate 40, and the irradiation region 70. As described above, since the detection region 74 according to this embodiment is determined by the height H of the breast WB compressed by the compression plate 40, the size of the detection region 74 changes depending on the breast WB and a compressed state of the breast WB. In addition, in this embodiment, it is assumed that the thickness of the bottom portion 43 is ignored for convenience since the thickness of the bottom portion 43 is relatively small.

For example, first, the detection unit 64 according to this embodiment acquires the thickness H of the breast WB compressed by the compression plate 40 in order to derive the detection region 74. Further, the method by which the detection unit 64 acquires the thickness H of the breast WB is not limited. For example, a detection unit that detects the amount of movement of the compression plate 40 by the compression plate driving unit (not illustrated) provided in the compression unit 36 of the compression plate 40 may be provided, and the detection unit 64 may acquire the thickness of the breast WB derived from the amount of movement of the compression plate 40 detected by the detection unit. Furthermore, for example, a sensor or the like for detecting the height from the imaging surface 30A to the compression plate 40, that is, the thickness H of the breast WB may be provided in the mammography apparatus 10 or the like, and the detection unit 64 may acquire the thickness H detected by the sensor. Moreover, for example, a marker or the like may be provided on a region which does not overlap the breast WB, such as an end portion of the compression plate 40, the distance between the TOF camera 39 and the marker may be measured on the basis of an image of the marker included in the distance image, and the distance between the TOF camera 39 and the marker may be subtracted from the distance between the TOF camera 39 and the imaging surface 30A to acquire the thickness H of the breast WB.

The detection unit 64 subtracts the thickness H of the breast WB from the distance between the radiation source 37R and the imaging surface 30A to derive the distance between the radiation source 37R and the bottom portion 43. In addition, the detection unit 64 extracts a rectangular pyramid that has the radiation source 37R as the apex, the bottom portion 43 as the base, and the length of a perpendicular line as the distance between the radiation source 37R and the bottom portion 43 to derive the detection region 74 in the irradiation region 70.

Further, the detection unit 64 detects whether or not a foreign object is present in the detection region 74 on the basis of the distance between each position in the detection region 74 derived on the basis of the position of the detection region 74 and the TOF camera 39 and an image corresponding to the detection region 74 in the distance image acquired from the TOF camera 39. Specifically, since the position where the TOF camera 39 is disposed, specifically, the three-dimensional coordinates of the TOF camera 39 are known in advance, the distance between a position in the detection region 74 and the TOF camera 39 is obtained. More specifically, it is possible to obtain a pixel value (hereinafter, referred to as a pixel value of the detection region 74) in a case in which a position in the detection region 74 is represented by a distance image. In a case in which an object is present in the detection region 74, the pixel value of a pixel indicating the distance to the object in the distance image is any of the pixel values of each position in the detection region 74.

Figure 7B:
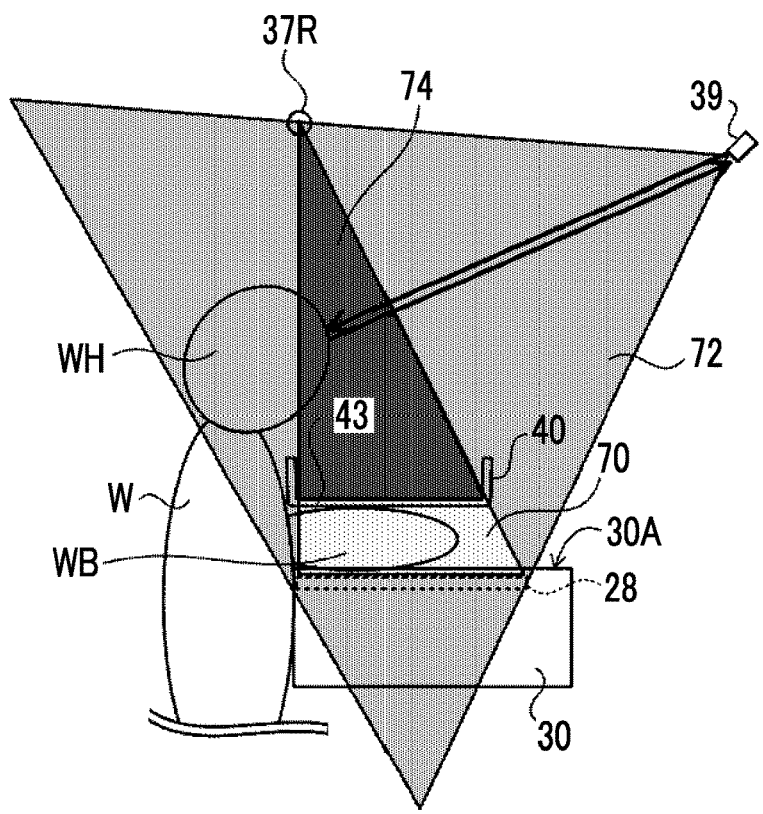
FIG. 7B is a diagram illustrating a case in which a foreign object is present in the detection region.

FIG. 7B illustrates an example of a state in which the head WH of the subject W enters the detection region 74 as the foreign object. In the example illustrated in FIG. 7B, the pixel value of the image corresponding to the detection region 74 in the distance image captured by the TOF camera 39 is a pixel value in which the distance measured by infrared rays reflected by the head WH in the detection region 74 has been reflected. Therefore, the detection unit 64 compares the pixel value of the image corresponding to the detection region 74 in the distance image acquired from the TOF camera 39 with the pixel value of each position in the detection region 74. In a case in which the pixel value of the image corresponding to the detection region 74 in the distance image is any of the pixel values of each position in the detection region 74, the detection unit 64 determines that a foreign object is present in the detection region 74. In this case, the detection unit 64 outputs a detection result indicating that a foreign object is present. On the other hand, in a case in which the pixel value of the image corresponding to the detection region 74 in the distance image acquired from the TOF camera 39 is not any of the pixel values of each position in the detection region 74, the detection unit 64 determines that a foreign object is absent in the detection region 74. In addition, in this embodiment, in a case in which it is determined that a foreign object is absent in the detection region 74, the detection unit 64 does not output the detection result. However, unlike this embodiment, the detection unit 64 may output a detection result indicating that a foreign object is absent.

Next, the operation of the console 12 according to this embodiment will be described with reference to the drawings.

Figure 8:
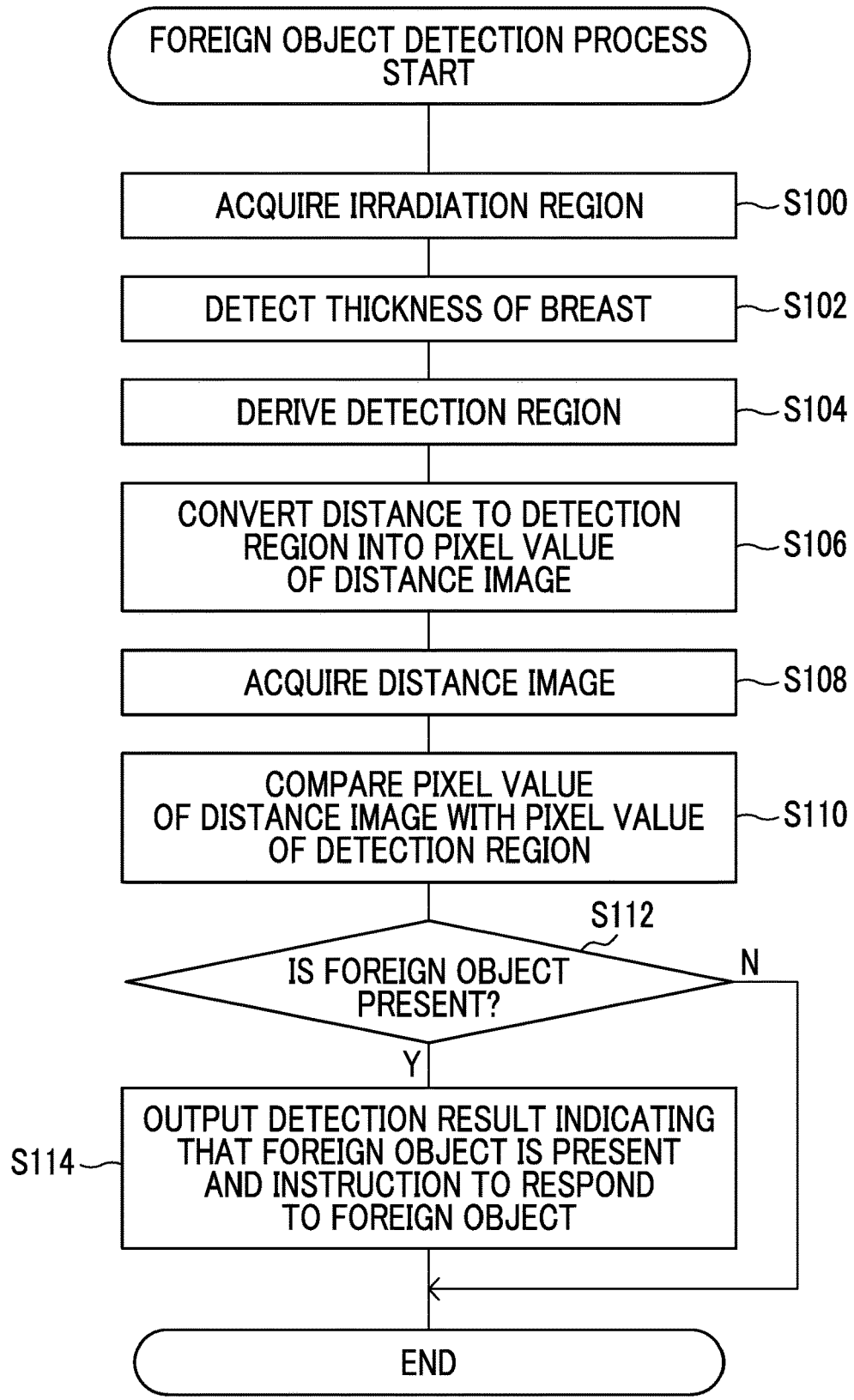
FIG. 8 is a flowchart illustrating an example of the flow of a foreign object detection process of a console according to the first embodiment.

In the console 12 according to this embodiment, the CPU 50A of the control unit 50 executes the foreign object detection processing program 51 stored in the ROM 50B to perform a foreign object detection process whose example is illustrated in FIG. 8. FIG. 8 is a flowchart illustrating an example of the flow of the foreign object detection process performed in the console 12 according to this embodiment. In addition, the timing when the CPU 50A performs the foreign object detection process is not limited and may be any timing. For example, the CPU 50A performs the foreign object detection process at the timing when the movement of the compression plate 40 is stopped, the timing when an instruction to emit the radiation R is received, or the like.

In Step S100 of FIG. 8, the first acquisition unit 60 acquires the information indicating the irradiation region 70 as described above. Then, in Step S102, the detection unit 64 acquires the thickness H of the breast WB as described above. Then, in Step S104, the detection unit 64 derives the detection region 74 on the basis of the information indicating the irradiation region 70 and the thickness H of the breast WB as described above.

Then, in Step S106, the detection unit 64 converts the distance from the TOF camera 39 to each position in the detection region 74 into the pixel value of the distance image. Specifically, the detection unit 64 converts the distance between the TOF camera 39 and each position in the detection region 74 into the pixel value of the distance image to derive the pixel value of each position in the detection region 74. Then, in Step S108, the second acquisition unit 62 acquires the distance image from the TOF camera 39 as described above.

Then, in Step S110, the detection unit 64 compares the pixel value of the image corresponding to the detection region 74 in the distance image acquired from the TOF camera 39 with the pixel value of each position of the detection region 74 as described above. Then, in Step S112, the detection unit 64 determines whether or not a foreign object is present in the detection region 74. As described above, in a case in which the pixel value of the image corresponding to the detection region 74 in the distance image is any of the pixel values of each position of the detection region 74, the detection unit 64 determines that a foreign object is present in the detection region 74. In a case in which the detection unit 64 determines that a foreign object is present, the determination result in Step S112 is "Yes", and the process proceeds to Step S114.

In Step S114, the detection unit 64 outputs the detection result indicating that a foreign object is present and an instruction to respond to the foreign object. In addition, the output destination of the detection result and the like is not particularly limited and may be the display unit 58 of the console 12 or the display unit (not illustrated) of the mammography apparatus 10. Further, the detection result and the like may be output to a plurality of output destinations. Furthermore, the instruction to respond to the foreign object is not limited. An example of the instruction is an instruction to prohibit the emission of the radiation R by the radiation source 36R. Moreover, an example of the instruction is an instruction to output information for warning the user that a foreign object is present in the detection region 74. In a case in which the warning is issued in this way, a warning method is not limited. For example, in addition to displaying the warning on the display unit 58, the warning may be issued by sound, light, or the like. In addition, the present disclosure is not limited to this embodiment. For example, the detection unit 64 may further output information indicating the position, size, and the like of the foreign object present in the detection region 74. The position, size, and the like of the foreign object can be specified from the position of a pixel corresponding to the pixel value of the detection region 74 among the pixels of the image corresponding to the detection region 74 in the distance image. Further, the type of the foreign object may be determined on the basis of the position, size, and the like of the detected foreign object, and information indicating the determined type of the foreign object may be output. Furthermore, a method for determining the type of the foreign object on the basis of the position, size, and the like of the detected foreign object is not particularly limited. Image analysis, such as template matching, using an image indicating the foreign object on the basis of the assumed foreign object or a trained model that has been trained by machine learning using images indicating various assumed foreign objects may be used.

In a case in which the process in Step S114 ends in this way, the foreign object detection process illustrated in FIG. 8 ends. In addition, in a case in which the detection unit 64 determines that a foreign object is absent, the determination result in Step S112 is "No", and the foreign object detection process illustrated in FIG. 8 ends.

As described above, in the console 12 according to this embodiment, it is possible to detect whether or not a foreign object is present in the detection region 74 on the basis of the distance image captured by the TOF camera 39. Therefore, according to the console 12 of this embodiment, even after positioning is ended by the user or even in a case in which it is difficult for the user to see the irradiation region 70 of the radiation R, it is possible to appropriately detect whether or not a foreign object other than the object to be imaged is present in the irradiation region 70 of the radiation R.

Figure 9A:
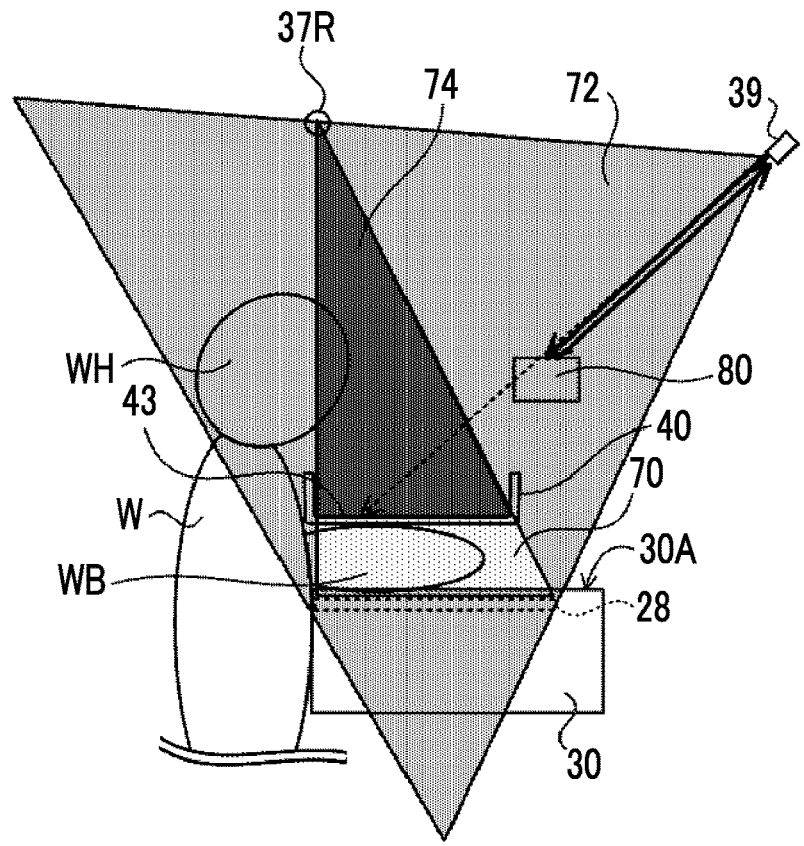
FIG. 9A is a diagram illustrating a case in which a foreign object is present between the detection region and the TOF camera.

In addition, in the foreign object detection process, in a case in which a foreign object 80 is present between the detection region 74 and the TOF camera 39 as illustrated in FIG. 9A, the infrared rays emitted from the TOF camera 39 do not reach a shadow region of the foreign object 80. Therefore, even in a case in which a foreign object is present in a region which is a shadow of the foreign object 80 in the detection region 74, it may be difficult to detect the foreign object. In this case, as in the case in which it is detected whether or not a foreign object is present in the detection region 74, it may be detected whether or not a foreign object is present in the region between the detection region 74 and the TOF camera 39. In a case in which it is detected that a foreign object is present, information or a warning indicating the fact may be output.

Figure 9B:
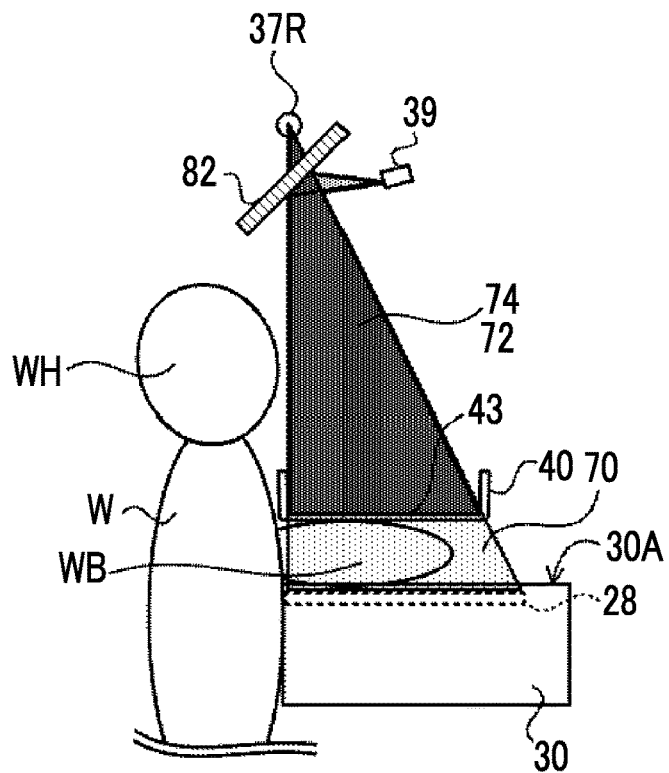
FIG. 9B is a diagram illustrating an aspect in which an imageable region of the TOF camera and the irradiation region are matched with each other.

Further, in the above-described embodiment, the aspect in which the irradiation region 70 of the radiation source 37R is different from the imageable region 72 of the TOF camera 39 has been described. However, as illustrated in FIG. 9B, the imageable region 72 of the TOF camera 39 may be substantially the same as the irradiation region 70 of the radiation source 37R. In the example illustrated in FIG. 9B, a mirror 82 provided in the mammography apparatus 10 reflects the infrared rays emitted from the TOF camera 39 and the infrared rays, which have been reflected by the object to be imaged or a foreign object and returned to the TOF camera 39, such that the imageable region 72 is substantially the same as the irradiation region 70. In addition, the mirror 82 may be retracted outside the irradiation region 70 in a case in which a radiographic image is captured. Further, in a case in which a material that transmits the radiation R, for example, a filter used to capture a radiographic image is used as the mirror 82, the radiographic image may be captured while the material or the filter is disposed in the irradiation region 70 without being retracted.

Second Embodiment

In the first embodiment, the aspect has been described in which it is detected whether or not a foreign object is present in the detection region 74 using the distance image captured by the TOF camera 39. In contrast, in this embodiment, an aspect will be described in which it is detected whether or not a foreign object is present in the detection region 74 using a visible light image captured by a visible light camera. In addition, for a mammography apparatus 10 and a console 12 according to this embodiment, the detailed description of the same configurations and operations as those in the first embodiment will not be repeated.

Figure 10:
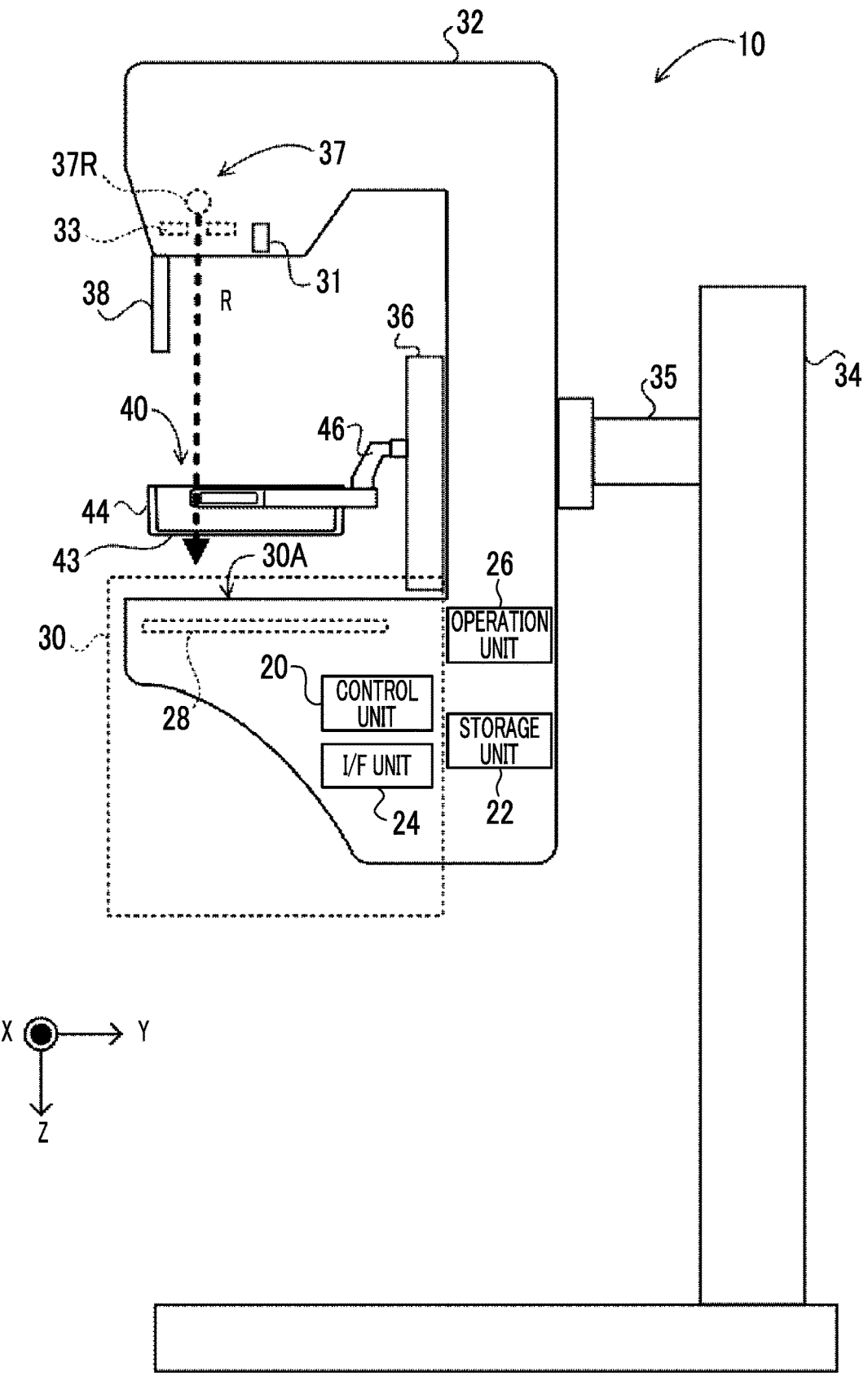
FIG. 10 is a side view illustrating an example of the outward appearance of a mammography apparatus according to a second embodiment.

FIG. 10 is a side view illustrating an example of the outward appearance of the mammography apparatus 10 according to this embodiment. As illustrated in FIG. 10, the mammography apparatus 10 according to this embodiment comprises a visible light camera 31 instead of the TOF camera 39 comprised in the mammography apparatus 10 according to the first embodiment.

The visible light camera 31 is a so-called general camera and captures a visible light image. The visible light camera 31 according to this embodiment is an example of the imaging device and a visible light image capture device according to the present disclosure. Specifically, the visible light camera 31 receives visible light reflected by the object to be imaged and captures a visible light image on the basis of the received visible light. As illustrated in FIG. 10, the visible light camera 31 according to this embodiment is provided in the vicinity of the collimator 33 of the radiation emitting unit 37, and an imageable region of the visible light camera 31 includes the detection region 74.

Since the overall configuration (see FIG. 5) of the console 12 according to this embodiment is the same as that in the first embodiment, the description of the overall configuration will not be repeated. On the other hand, since the functional configuration of the console 12 is different from that in the first embodiment, the functional configuration will be described. The console 12 according to this embodiment comprises a first acquisition unit 60, a second acquisition unit 62, and a detection unit 64, similarly to the console 12 (see FIG. 6) according to the first embodiment.

The function of the first acquisition unit 60 is the same as that in the first embodiment. On the other hand, the function of the second acquisition unit 62 is different from that in the first embodiment. The second acquisition unit 62 according to this embodiment has a function of acquiring the visible light image captured by the visible light camera 31. For example, the second acquisition unit 62 according to this embodiment acquires image data indicating the visible light image captured by the visible light camera 31 from the visible light camera 31 through the I/F unit 24 and the I/F unit 54. The visible light image acquired by the second acquisition unit 62 is output to the detection unit 64.

Further, the detection unit 64 according to this embodiment has a function of detecting whether or not a foreign object other than the object to be imaged is present in the irradiation region 70 on the basis of the visible light image.

For example, the detection unit 64 according to this embodiment derives a space between the object to be imaged and the radiation source 37R as the detection region 74 in the irradiation region 70 and detects whether or not a foreign object is present in the derived detection region 74, similarly to the detection unit 64 according to the first embodiment.

In this embodiment, a visible light image captured by the visible light camera 31 in a case in which a foreign object is absent in the detection region 74 is obtained as a reference visible light image in advance. In addition, a device for storing the reference visible light image is not limited. For example, the reference visible light image may be stored in the storage unit 22 of the mammography apparatus 10 or the storage unit 52 of the console 12. The detection unit 64 compares an image corresponding to the detection region 74 in the visible light image acquired from the visible light camera 31 with an image corresponding to the detection region 74 in the reference visible light image. Specifically, a difference between the pixel values of each image is derived to perform the comparison. In a case in which a foreign object is present in the detection region 74, the image corresponding to the detection region 74 in the visible light image acquired from the visible light camera 31 includes the image of the foreign object. Therefore, there is a large difference between the pixel value of the pixel corresponding to the image of the foreign object and the pixel value of the pixel at the same position in the reference visible light image. Therefore, the detection unit 64 determines that a foreign object is present in the detection region 74 in a case in which there is a region in which a predetermined number or more of pixels, in which the absolute value of the difference between the pixel value of the image corresponding to the detection region 74 in the visible light image acquired from the visible light camera 31 and the pixel value of the image corresponding to the detection region 74 in the reference visible light image is larger than a foreign object detection threshold value, are continuous.

In addition, since the operation of the console 12 according to this embodiment, specifically, the foreign object detection process is different from that in the first embodiment, the foreign object detection process performed by the console 12 according to this embodiment will be described.

Figure 11:
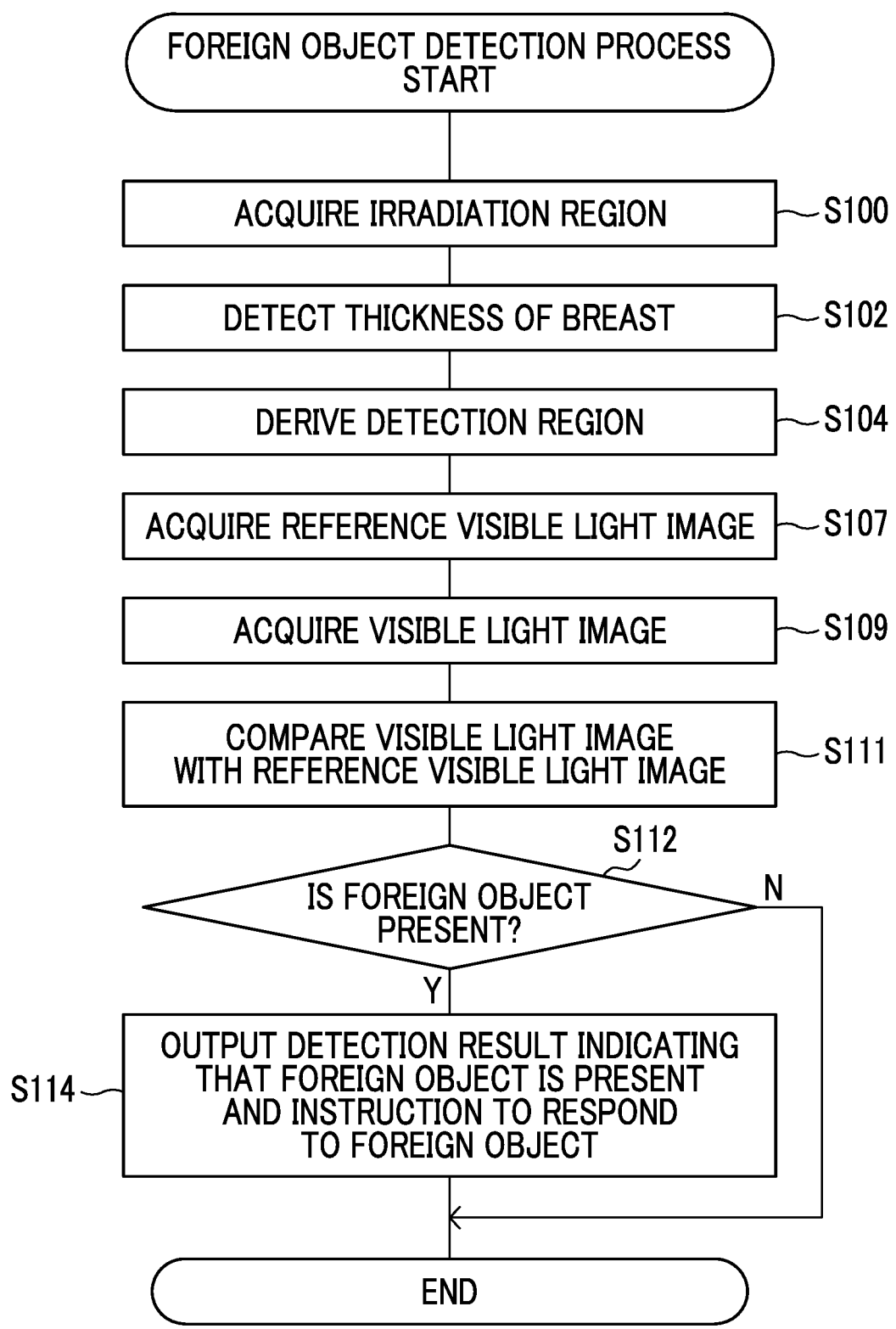
FIG. 11 is a flowchart illustrating an example of the flow of a foreign object detection process of a console according to the second embodiment.

FIG. 11 is a flowchart illustrating an example of the flow of the foreign object detection process performed in the console 12 according to this embodiment. As illustrated in FIG. 11, the foreign object detection process according to this embodiment includes processes in Steps S107 to S111 instead of Steps S106 to S110 in the foreign object detection process (see FIG. 8) according to the first embodiment.

In Step S107, the detection unit 64 acquires the reference visible light image as described above. Then, in Step S109, the second acquisition unit 62 acquires a visible light image from the visible light camera 31 as described above. Then, in Step S111, the detection unit 64 compares the visible light image with the reference visible light image as described above. Then, in Step S112, the detection unit 64 determines whether or not a foreign object is present in the detection region 74 on the basis of the comparison result in Step S111.

As described above, in the console 12 according to this embodiment, it is possible to detect whether or not a foreign object is present in the detection region 74 on the basis of the visible light image captured by the visible light camera 31. Therefore, according to the console 12 of this embodiment, even after positioning is ended by the user or even in a case in which it is difficult for the user to see the irradiation region 70 of the radiation R, it is possible to appropriately detect whether or not a foreign object other than the object to be imaged is present in the irradiation region 70 of the radiation R.

In addition, the first embodiment and this embodiment may be combined. In other words, it may be detected whether or not a foreign object is present in the irradiation region 70 using the distance image captured by the TOF camera 39 and the visible light image captured by the visible light camera 31. In this case, for example, in a case in which at least one of the detection result using the distance image captured by the TOF camera 39 or the detection result using the visible light image captured by the visible light camera 31 shows that a foreign object is present, the detection unit 64 may give an instruction to respond to the foreign object and the like (see Step S114 of the foreign object detection process in FIG. 8). Further, for example, the irradiation region 70 may be imaged in different directions by the TOF camera 39 and the visible light camera 31, and a foreign object may be detected in different directions.

Third Embodiment

In this embodiment, another aspect will be described in which it is detected whether or not a foreign object is present in the irradiation region 70 of the radiation R using the visible light image captured by the visible light camera 31. In addition, for a mammography apparatus 10 and a console 12 according to this embodiment, the detailed description of the same configurations and operations as those in the first and second embodiments will not be repeated.

Figure 12:
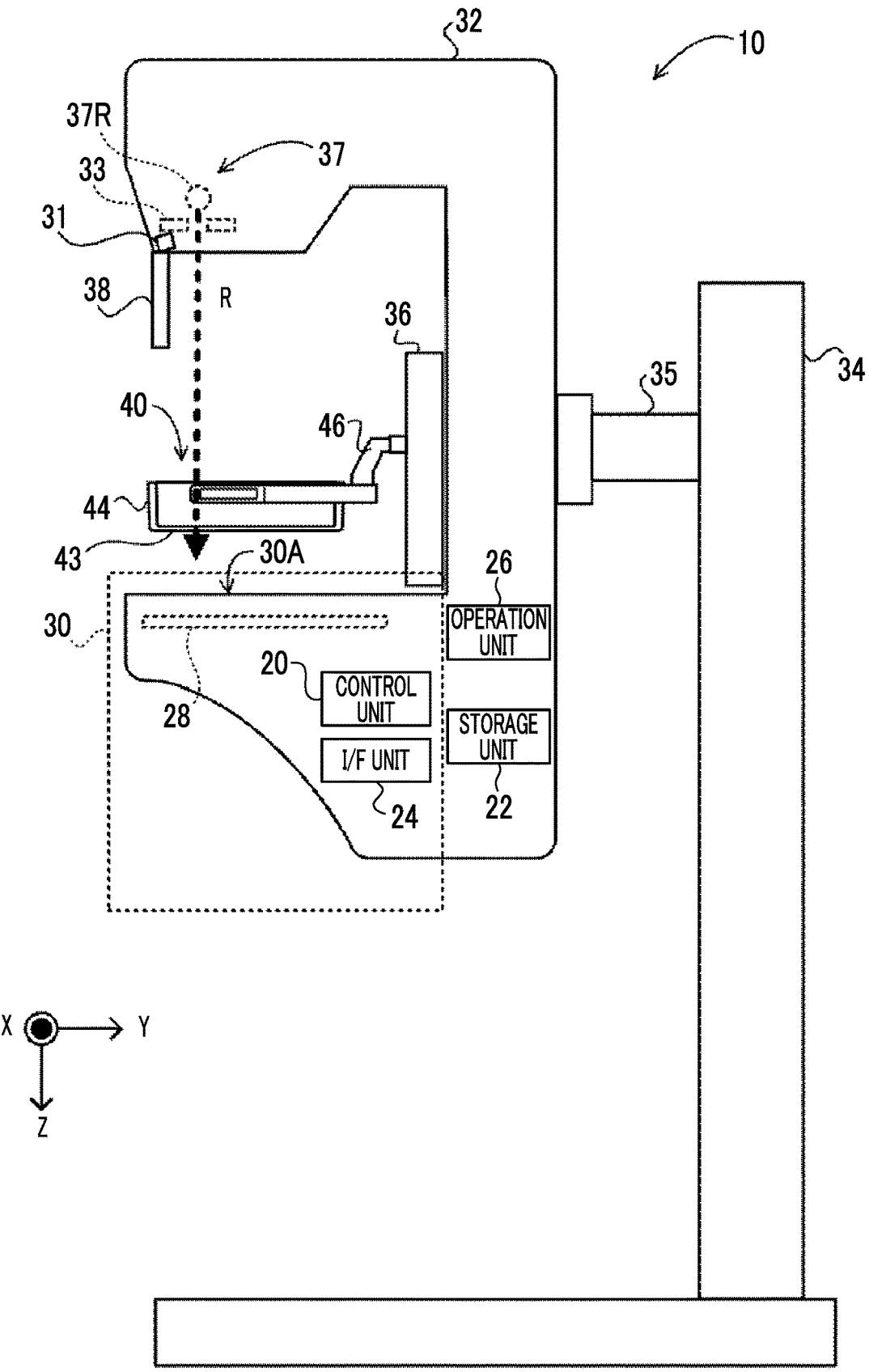
FIG. 12 is a side view illustrating an example of the outward appearance of a mammography apparatus according to a third embodiment.
Figure 13:
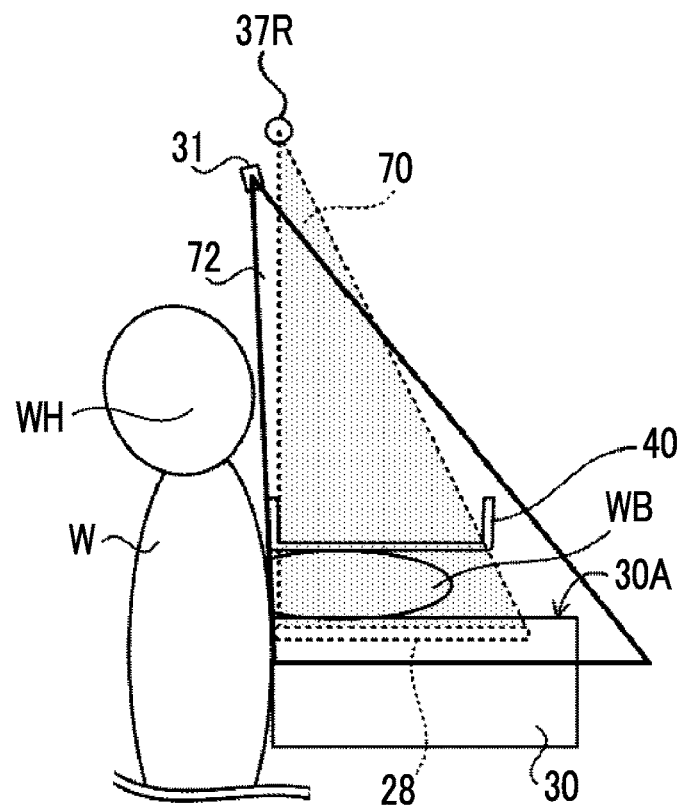
FIG. 13 is a diagram illustrating an imageable region of a visible light camera.

FIG. 12 is a side view illustrating an example of the outward appearance of the mammography apparatus 10 according to this embodiment. As illustrated in FIG. 12, the mammography apparatus 10 according to this embodiment is different from the mammography apparatus 10 (see FIG. 10) according to the second embodiment in the position where the visible light camera 31 is provided. As illustrated in FIG. 12, the visible light camera 31 according to this embodiment is provided on the side of the radiation emitting unit 37 which faces the subject W. As illustrated in FIG. 13, the imageable region 72 of the visible light camera 31 according to this embodiment includes the irradiation region 70 and also includes a region in which the compression plate 40 is provided. Further, for the imageable region 72 of the visible light camera 31 according to this embodiment, a region which is close to the chest wall in the breast WB of the subject W is defined as the imageable region.

Figure 14:
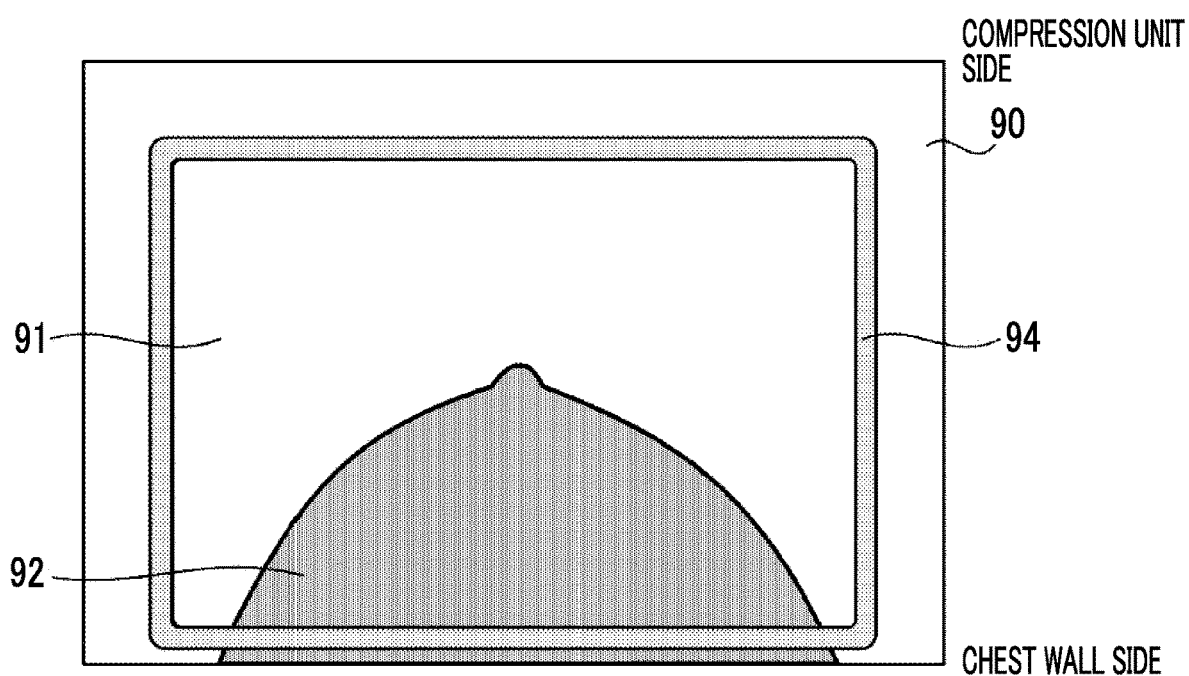
FIG. 14 is a diagram illustrating an example of a visible light image captured by the visible light camera.

FIG. 14 illustrates an example of a visible light image 90 captured by the visible light camera 31 according to this embodiment. As illustrated in FIG. 14, the visible light image 90 captured by the visible light camera 31 includes an image corresponding to the compression plate 40. Specifically, since the bottom portion 43 of the compression plate 40 according to this embodiment is made of a transparent material, a breast image 92 of the breast WB is included in a bottom portion region 91 of the visible light image 90 which corresponds to the bottom portion 43 of the compression plate 40. Further, as illustrated in FIG. 14, the visible light image 90 includes an edge image 94 corresponding to an edge portion of the compression plate 40. In addition, in this embodiment, the edge image 94 is an image including the wall portion 44 of the bottom portion 43. As described above, in this embodiment, the image of the wall portion 44 of the compression plate 40 is applied as the edge image 94. Therefore, it is preferable that the wall portion 44 of the compression plate 40 is more likely to be included in the visible light image 90 than the bottom portion 43. For example, it is preferable that the bottom portion 43 and the wall portion 44 are processed to be distinguishable from each other in the visible light image 90. In other words, it is preferable that the edge portion of the compression plate 40 is more highlighted than the surroundings. The wall portion 44 may be made of a material that is likely to be included in the visible light image 90. Specifically, at least one of a material having a color different from that of the imaging table 30 or the breast WB, a phosphorescent material, or a fluorescent material may be used as the material forming the wall portion 44. Further, for example, the side of the wall portion 44 of the compression plate 40 which faces the radiation source 37R may be configured to be likely to be included in the visible light image 90. Specifically, at least one of a material having a color different from that of the imaging table 30 or the breast WB, a phosphorescent material, or a fluorescent material may be applied or attached to a surface of the wall portion 44 which faces the radiation source 37R. In addition, various methods, such as painting, member attachment, the coloring of the material forming the compression member, and surface treatment, can be adopted. Even in a case in which the bottom portion 43 and the wall portion 44 are made of materials having the same color, the apparent colors thereof may change depending on the thickness thereof.

Figure 15:
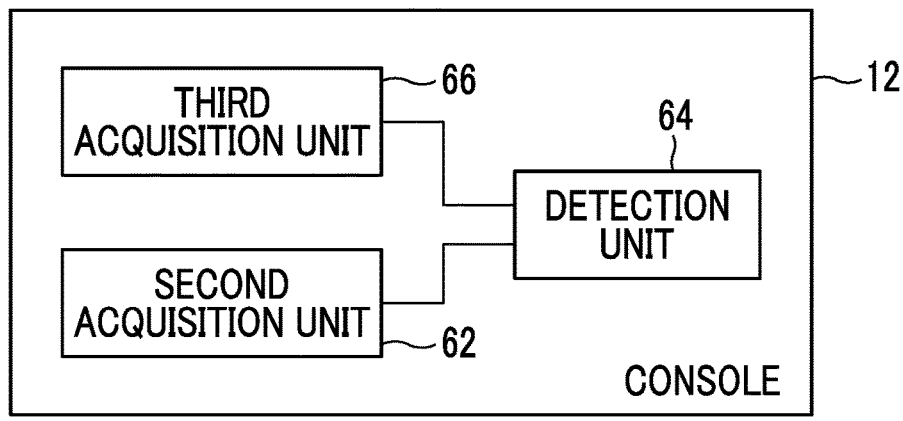
FIG. 15 is a functional block diagram illustrating an example of a functional configuration of a console according to the third embodiment.

Since the overall configuration (see FIG. 5) of the console 12 according to this embodiment is the same as that in the first and second embodiments, the description of the overall configuration will not be repeated. On the other hand, since the functional configuration of the console 12 is different from that in the first and second embodiments, the functional configuration will be described. FIG. 15 is a functional block diagram illustrating an example of the functional configuration of the console 12 according to this embodiment. As illustrated in FIG. 15, the console 12 according to this embodiment is different from the console 12 (see FIG. 6) according to each of the above-described embodiments in that it comprises a third acquisition unit 66 instead of the first acquisition unit 60.

The third acquisition unit 66 has a function of acquiring compression member information indicating the type of the compression plate 40 attached to the compression unit 36. As described above, there are a plurality of types of compression plates 40 including a compression plate 40 used for spot imaging that can be attached to the mammography apparatus 10. The size of the bottom portion 43 of the compression plate 40 according to this embodiment is determined according to the type of the compression plate 40. Therefore, the position and size of the edge image 94 included in the visible light image 90 are determined according to the type of the compression plate 40 attached to the compression unit 36.

For example, a compression plate identifier (not illustrated) for identifying the type of the compression plate 40 is provided on the side of the support portion 46 of the compression plate 40 which is attached to the compression unit 36 according to this embodiment. Further, the compression unit 36 is provided with an identifier sensor (not illustrated). The identifier sensor reads the compression plate identifier provided in the support portion 46 of the compression plate 40. The third acquisition unit 66 acquires the compression plate identifier read by the identifier sensor as the compression member information through the I/F unit 24 and the I/F unit 54. The compression member information acquired by the third acquisition unit 66 is output to the detection unit 64.

In addition, the method by which the third acquisition unit 66 according to this embodiment acquires the compression member information is not limited to the above-described aspect. For example, in a case in which the type of the compression plate 40 used for imaging is determined for each type of imaging, the third acquisition unit 66 may acquire the type of imaging as the compression member information from an imaging menu or the like.

Further, the detection unit 64 according to this embodiment has a function of detecting whether or not a foreign object other than the object to be imaged is present in the irradiation region 70 on the basis of the visible light image, similarly to the detection unit 64 according to the second embodiment. However, the content of a process required for the detection is different.

Figure 16:
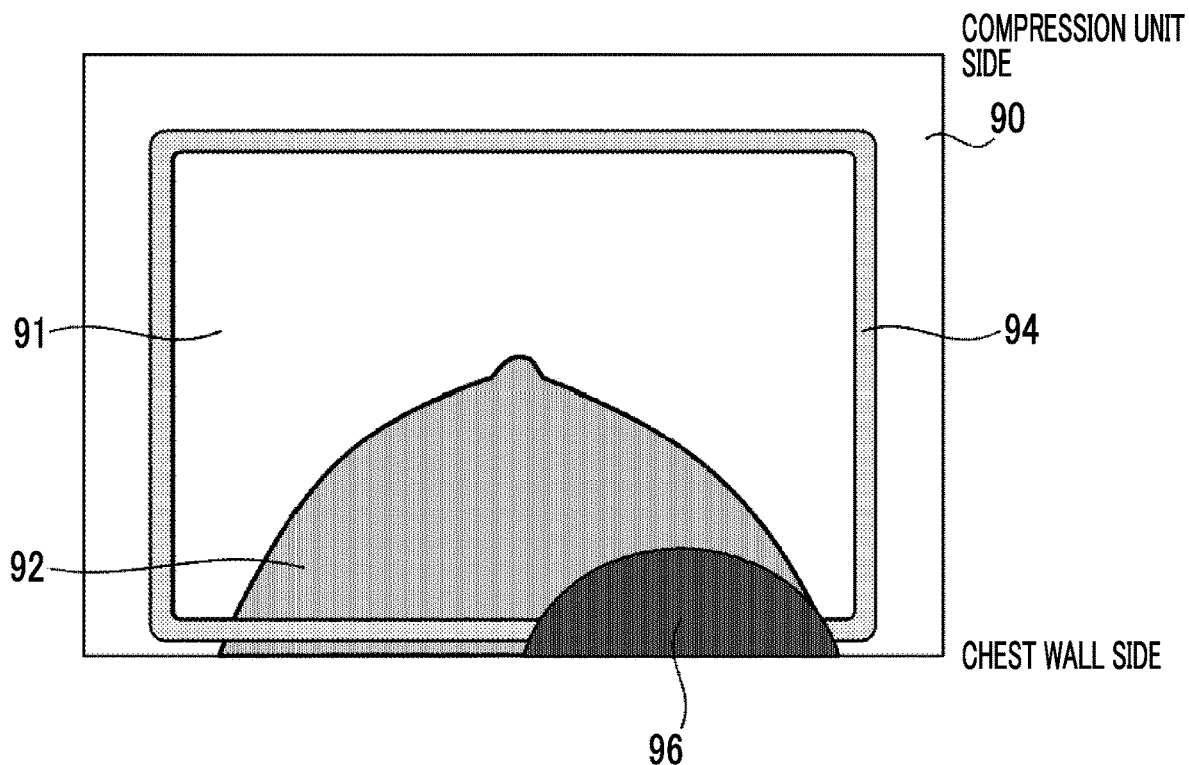
FIG. 16 is a diagram illustrating an example of a visible light image captured by the visible light camera in a case in which a foreign object is present in the irradiation region.

In a case in which a foreign object enters the irradiation region 70 as described above, the foreign object may be present from the outside of the irradiation region 70 to the inside of the irradiation region 70 like the head WH of the subject W described with reference to FIG. 7B. In a case in which the foreign object is present from the outside of the irradiation region 70 to the inside of the irradiation region 70, the foreign object is present beyond the edge portion of the compression plate 40. In this case, as illustrated in FIG. 16, a foreign object image 96 corresponding to the foreign object included in the visible light image 90 is present on the edge image 94. In other words, the edge image 94 included in the visible light image 90 in a case in which a foreign object is present is chipped by the foreign object image 96. Therefore, the detection unit 64 according to this embodiment extracts the edge image 94 from the visible light image 90 and determines that a foreign object is present in the irradiation region 70 in a case in which the extracted edge image 94 is chipped. On the other hand, the detection unit 64 extracts the edge image 94 from the visible light image 90, and determines that a foreign object is absent in the irradiation region 70 in a case in which the extracted edge image 94 is not chipped.

In addition, since the operation of the console 12 according to this embodiment, specifically, the foreign object detection process is different from that in the first and second embodiments, the foreign object detection process performed by the console 12 according to this embodiment will be described.

Figure 17:
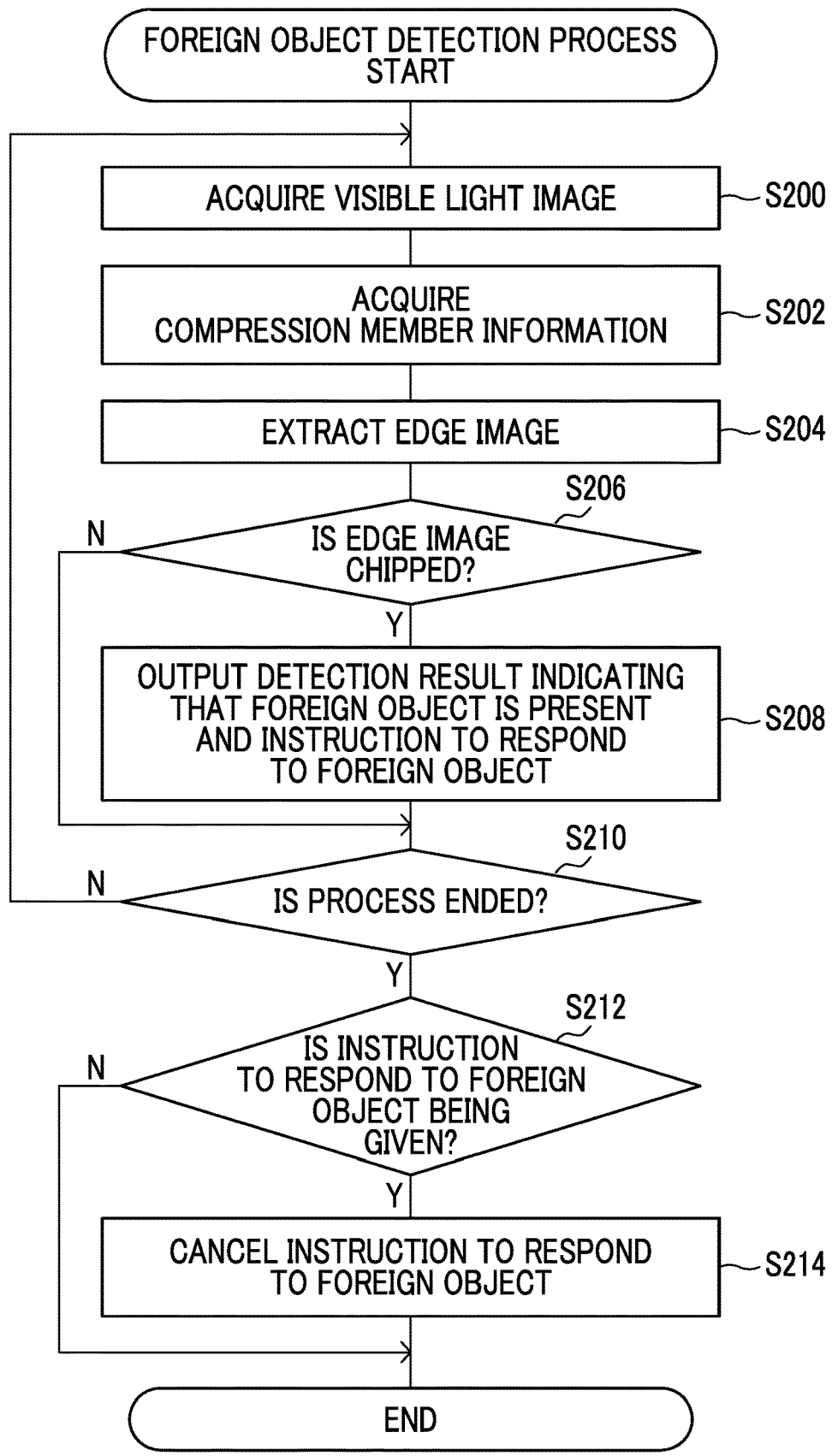
FIG. 17 is a flowchart illustrating an example of the flow of a foreign object detection process of the console according to the third embodiment.

FIG. 17 is a flowchart illustrating an example of the flow of the foreign object detection process performed in the console 12 according to this embodiment.

In Step S200, the second acquisition unit 62 acquires the visible light image 90 from the visible light camera 31 as described above. Then, in Step S202, the third acquisition unit 66 acquires the compression member information as described above.

Then, in Step S204, the detection unit 64 extracts the edge image 94 from the visible light image 90 acquired in Step S200 on the basis of the compression member information acquired in Step S202 as described above. In addition, the specific method by which the detection unit 64 extracts the edge image 94 from the visible light image 90 is not particularly limited. For example, the detection unit 64 may apply the existing image processing for edge detection to extract the edge image 94. Further, for example, the detection unit 64 stores typical pattern data of the edge image 94 as a template in advance and derives similarity to pattern data while searching for the visible light image 90 with a template. Then, the detection unit 64 may apply template matching, in which the edge image 94 is considered to be present at a position where the similarity is equal to or greater than a reference value and is the maximum, to extract the edge image 94.

Further, for example, in a case in which the wall portion 44 of the compression plate 40 has a color different from that of the surroundings as described above or in a case in which a phosphorescent material is used, the color of the edge image 94 included in the visible light image 90 is known in advance. Therefore, a region that has a known color and is formed by a predetermined number or more of pixels may be extracted as the edge image 94. In addition, the detection unit 64 according to this embodiment estimates the shape and size of the edge image 94 according to the type of the compression plate 40 indicated by the compression member information and uses the estimated shape and size to extract the edge image 94. The estimation of the shape and size of the edge image 94 according to the type of the compression plate 40 indicated by the compression member information makes it possible to extract the edge image 94 with higher accuracy and to reduce a processing load on an extraction process.

Then, in Step S206, the detection unit 64 determines whether or not the edge image 94 extracted in Step S204 is chipped. For example, the detection unit 64 according to this embodiment compares the edge image 94 with a reference edge image to determine whether or not the edge image 94 is chipped. In this embodiment, the visible light image 90 or the edge image 94 captured by the visible light camera 31 in a case in which a foreign object is absent in the irradiation region 70 is obtained as the reference edge image in advance. In addition, a device that stores the reference edge image is not limited. For example, the reference edge image may be stored in the storage unit 22 of the mammography apparatus 10 or the storage unit 52 of the console 12. The detection unit 64 compares the edge image 94 extracted in Step S204 with the reference edge image. Specifically, the comparison is performed by deriving a difference between the pixel values of the extracted edge image 94 and the reference edge image. More specifically, in a case in which there is a region in which a predetermined number or more of pixels, in which the absolute value of the difference between the pixel value of the extracted edge image 94 and the pixel value of the reference edge image is larger than a chipping detection threshold value, are continuous, it is determined that the edge image 94 is chipped. Further, the method by which the detection unit 64 determines whether or not the edge image 94 is chipped is not particularly limited. For example, the reference edge image may not be used, and the detection unit 64 may determine that the edge image 94 is chipped in a case in which a line that is the outer circumference of the compression plate 40 recognized by the edge image 94 is broken by a predetermined number of pixels or more.

In a case in which the edge image 94 is not chipped, the determination result in Step S206 is "No", and the process proceeds to Step S210. This corresponds to a case in which a foreign object is absent in the irradiation region 70. On the other hand, in a case in which the edge image 94 is chipped, the determination result in Step S206 is "Yes", and the process proceeds to Step S208. This corresponds to a case in which a foreign object is present in the irradiation region 70.

In Step S208, the detection unit 64 outputs the detection result indicating that a foreign object is present and an instruction to respond to the foreign object, as in S114 of the foreign object detection process (see FIGS. 8 and 11) according to the first and second embodiments and then proceeds to Step S210.

In Step S210, the detection unit 64 determines whether or not to end the foreign object detection process that is being performed. The detection unit 64 according to this embodiment determines to end the foreign object detection process in a case in which end conditions are satisfied. An example of the end conditions is a case in which the user inputs an instruction to emit the radiation R using the operation unit 56 or the like. Further, an example of the end conditions is a case in which the user inputs an instruction to end the foreign object detection process using the operation unit 56 or the like. In a case in which the end conditions are not satisfied, the determination result in Step S210 is "No", and the process returns to Step S200. Then, the processes in Steps S200 to S208 are repeated. For example, the user who has recognized that a foreign object is present in the irradiation region 70 corrects the posture of the subject W such that the foreign object does not enter the irradiation region 70. Therefore, the above-described process is repeated to continue to determine whether or not a foreign object is present in the irradiation region 70.

On the other hand, in a case in which the end conditions are satisfied, the determination result in Step S210 is "Yes", and the process proceeds to Step S212. In Step S212, the detection unit 64 determines whether or not an instruction to respond to the foreign object is being given. Specifically, it is determined whether or not the process in Step S208 has been performed. In a case in which the process in Step S208 has not been performed, that is, in a case in which a foreign object is absent in the irradiation region 70, the determination result in Step S212 is "No", and the foreign object detection process illustrated in FIG. 17 is ended. On the other hand, in a case in which the process in Step S208 has been performed, that is, in a case in which a foreign object is present in the irradiation region 70, the determination result in Step S212 is "Yes", and the process proceeds to Step S214.

In Step S214, the detection unit 64 cancels the instruction to respond to the foreign object given in Step S208. For example, in a case in which the detection unit 64 outputs information for warning the user that a foreign object is present in the detection region 74 as the instruction to respond to the foreign object, the output of the information for warning is stopped to cancel the warning. In a case in which the process in Step S214 ends, the foreign object detection process illustrated in FIG. 17 ends.

As described above, the console 12 according to this embodiment detects whether or not a foreign object is present in the irradiation region 70 on the basis of the chipping of the image of the compression plate 40 included in the visible light image 90 captured by the visible light camera 31, particularly, the chipping of the edge image 94. Therefore, according to the console 12 of this embodiment, even after positioning is ended by the user or even in a case in which it is difficult for the user to see the irradiation region 70 of the radiation R, it is possible to appropriately detect whether or not a foreign object other than the object to be imaged is present in the irradiation region 70 of the radiation R.

In addition, this embodiment is not limited to the above-described aspect. For example, the following modification examples can be applied.

Modification Example 1

In this modification example, instead of detecting whether or not the entire edge image 94 is chipped, the detection unit 64 detects whether or not a region of the edge image 94, which is likely to be chipped in a case in which a foreign object enters the irradiation region 70, is chipped.

In a case in which a foreign object enters the irradiation region 70, it often enters the irradiation region 70 from the chest wall side of the subject W like the head WH of the subject W illustrated in FIG. 7B. Therefore, as illustrated in FIG. 16, in many cases, the foreign object image 96 corresponding to the foreign object is included in the visible light image 90 at a position corresponding to the chest wall side of the subject W. Therefore, the detection unit 64 according to this modification example detects whether or not a region of the edge image 94 which corresponds to a side on the chest wall side of the subject W is chipped.

In addition, the region of the edge image 94, which is likely to be chipped in a case in which a foreign object enters the irradiation region 70, differs depending on the type of radiography. The mammography apparatus 10 can perform at least two types of imaging as the type of radiography. Specifically, the mammography apparatus 10 can perform at least two types of imaging, that is, cranio-caudal (CC) imaging in which an imaging direction is a cranio-caudal direction and medio-lateral oblique (MLO) imaging in which the imaging direction is a medio-lateral oblique direction on the breast WB.

Figure 18:
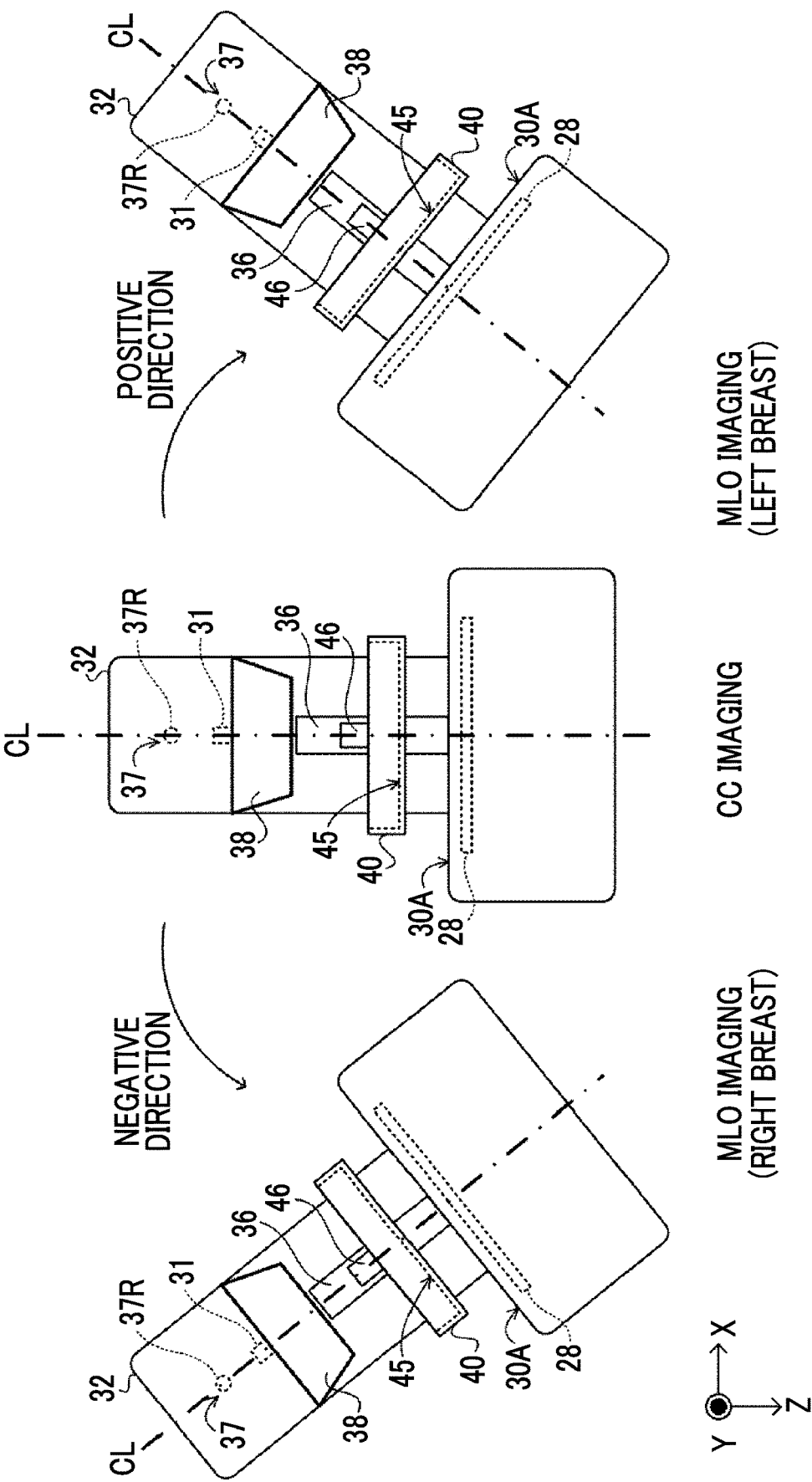
FIG. 18 is a diagram illustrating a state of the mammography apparatus in CC imaging and MLO imaging.

FIG. 18 illustrates an example of the state of the imaging table 30, the arm portion 32, and the radiation source 37R in the CC imaging and the MLO imaging. As illustrated in FIG. 18, in a case in which the CC imaging is performed, the imaging surface 30A is adjusted to face the upper side (the head WH of the subject W) of the mammography apparatus 10 in a state in which it faces the radiation source 37R. Therefore, the radiation R is emitted from the radiation source 37R to the breast WB in a direction from the head WH to the foot of the subject W, and the CC imaging is performed.

In a case in which the CC imaging is performed, as described above, the foreign object image 96 corresponding to the foreign object is often included in the visible light image 90 at a position corresponding to the chest wall side of the subject W. Therefore, the detection unit 64 according to this modification example detects whether or not the region of the edge image 94, which corresponds to the side on the chest wall side of the subject W, is chipped in a case in which the CC imaging is performed.

On the other hand, as illustrated in FIG. 18, in a case in which the MLO imaging is performed, the arm portion 32 is rotated up to a predetermined angle within the range of, for example, 45 degrees or more and less than 90 degrees in a negative direction or a positive direction with respect to the case in which the CC imaging is performed to be inclined with respect to the cranio-caudal direction of the subject W. Specifically, in a case in which the left breast is imaged, the arm portion 32 is inclined in the positive direction, with the imaging surface 30A and the radiation source 37R facing each other, such that the imaging surface 30A is inclined to the right.

In a case in which the left breast is imaged in the MLO imaging, the compression plate 40 is maintained in a state in which the left side is the upper side and the right side is the lower side as illustrated in FIG. 18. In addition, the left and right sides in this modification example correspond to the left and right sides of the subject W that faces the imaging table 30. In general, a foreign object tends to enter the irradiation region from the upper side of the inclined imaging table 30. Therefore, a foreign object tends to enter the irradiation region from a side which is the upper side of the compression plate 40. In a case in which the MLO imaging is performed on the left breast WB, the foreign object image 96 included in the visible light image 90 is often included at a position corresponding to the left side of the subject W in addition to the position corresponding to the chest wall side of the subject W. Therefore, the detection unit 64 according to this modification example detects whether or not the regions of the edge image 94 corresponding to each of the chest wall side and the left side of the subject W are chipped in a case in which the MLO imaging is performed on the left breast WB.

Further, in a case in which the right breast is imaged, the arm portion 32 is inclined in the negative direction, with the imaging surface 30A and the radiation source 37R facing each other, such that the imaging surface 30A is inclined to the left. Therefore, the radiation R is emitted from the radiation source 37R to the breast WB in a direction from the center of the body of the subject W to the outside (in a direction from a space between the breasts WB of the subject W to the arm), and the MLO imaging is performed.

In a case in which the right breast is imaged in the MLO imaging, the compression plate 40 is maintained in a state in which the right side is the upper side and the left side is the lower side as illustrated in FIG. 18. Therefore, contrary to the case of the left breast WB described above, in a case in which the MLO imaging is performed on the right breast WB, the foreign object image 96 included in the visible light image 90 is often included at a position corresponding to the right side of the subject W in addition to the position corresponding to the chest wall side of the subject W. Therefore, the detection unit 64 according to this modification example detects whether or not the regions of the edge image 94 corresponding to each of the chest wall side and the right side of the subject W are chipped in a case in which the MLO imaging is performed on the right breast WB.

Figure 19:
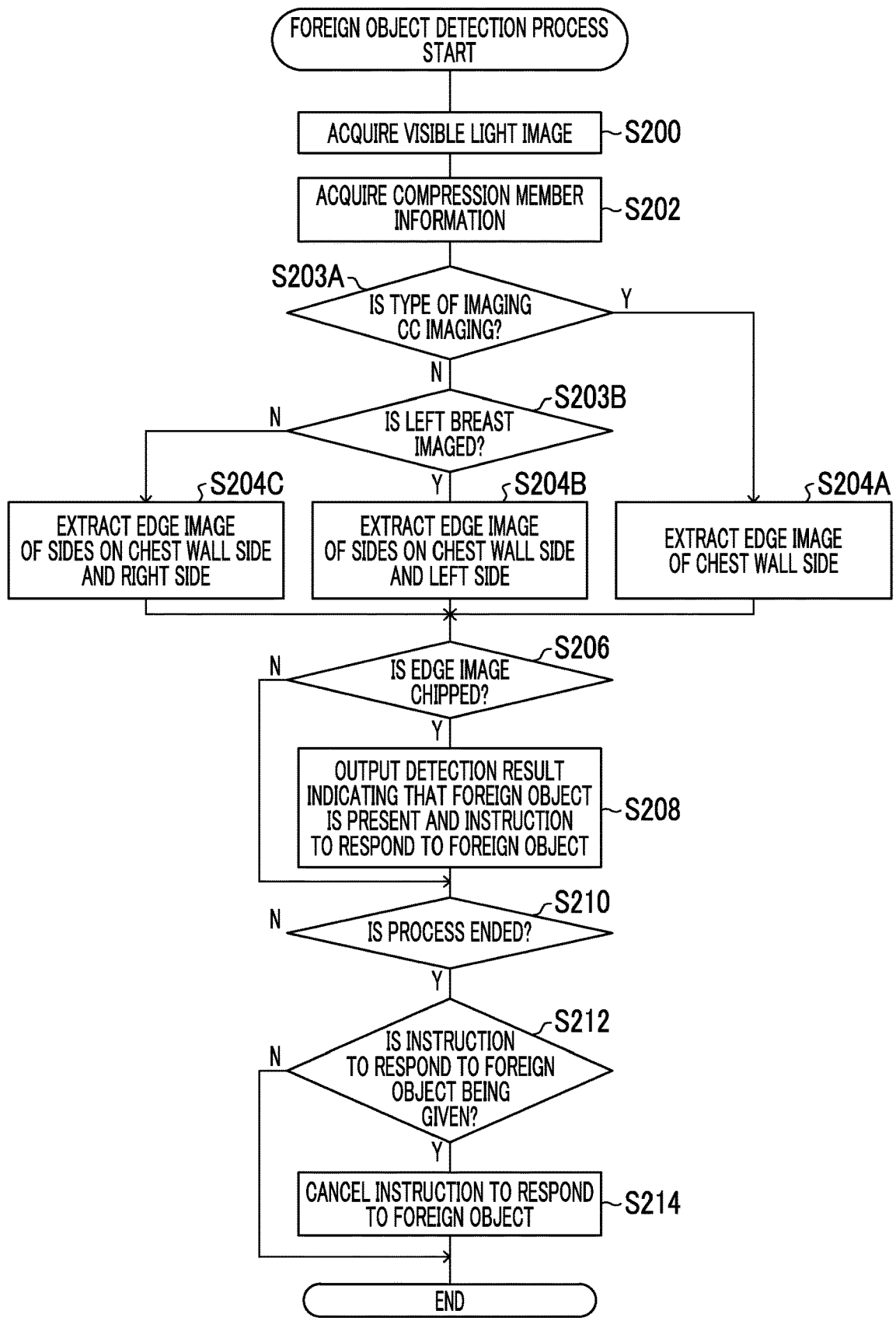
FIG. 19 is a flowchart illustrating an example of the flow of a foreign object detection process of the console according to Modification Example 1.

FIG. 19 is a flowchart illustrating an example of the flow of the foreign object detection process performed in the console 12 according to this modification example. The foreign object detection process according to this modification example illustrated in FIG. 19 is different from the foreign object detection process (see FIG. 17) according to the above-described embodiment in that it comprises processes in Steps S203A and S203B after Step S202 and comprises processes in Steps S204A to S204C instead of Step S204.

As illustrated in FIG. 19, in Step S203A, the detection unit 64 determines whether or not the type of imaging is the CC imaging. In addition, the method by which the detection unit 64 determines whether or not the type of imaging is the CC imaging is not particularly limited. For example, the type of imaging may be specified with reference to an imaging menu. Further, for example, since the angle of the arm portion 32 is different between the CC imaging and the MLO imaging, it may be determined whether or not the type of imaging is the CC imaging on the basis of the angle of the arm portion 32.

In a case in which the type of imaging is the CC imaging, the determination result in Step S203A is "Yes" and the process proceeds to Step S204A. As described above, in Step S204A, the detection unit 64 detects whether or not the region of the edge image 94 corresponding to a side on the chest wall side of the subject W is chipped and then proceeds to Step S206.

On the other hand, in a case in which the type of imaging is not the CC imaging, that is, in a case in which the type of imaging is the MLO imaging, the determination result in Step S203A is "No" and the process proceeds to Step S203B. In Step S203B, the detection unit 64 determines whether or not the left breast WB is imaged. In a case in which the left breast WB is imaged, the determination result in Step S203B is "Yes", and the process proceeds to Step S204B.

As described above, in Step S204B, the detection unit 64 detects whether or not the regions of the edge image 94 corresponding to sides on the chest wall side and the left side of the subject W are chipped and then proceeds to Step S206.

On the other hand, in a case in which the left breast WB is not imaged in Step S203B, that is, in a case in which the right breast WB is imaged, the determination result is "No", and the process proceeds to Step S204C. As described above, in Step S204C, the detection unit 64 detects whether or not the regions of the edge image 94 corresponding to the sides on the chest wall side and the right side of the subject W are chipped and then proceeds to Step S206.

As described above, according to this modification example, the entire edge image 94 is not used to detect whether or not a foreign object is present in the irradiation region 70. Therefore, it is possible to more quickly perform the foreign object detection process and to reduce the processing load.

In addition, in a case in which a phosphorescent material is used for the edge portion of the compression plate 40, it is preferable that the edge portion is irradiated with light for a predetermined period of time at a predetermined time interval to store the light, for example, in a state in which the subject W is not compressed by the compression plate 40, a state in which the radiation R is not emitted, and a state in which a compression thickness is not applied to the compression plate 40. Further, in a case in which light is emitted such that the phosphorescent material of the edge portion stores light, it is preferable that the compression plate 40 is located at a position away from the radiation source 37R. In other words, it is preferable to reduce the height of the compression plate 40.

Further, in this embodiment, the aspect has been described in which the chipping of the edge image 94 included in the visible light image 90 captured by the visible light camera 31 is detected to detect whether or not a foreign object is present in the irradiation region 70. However, as described above, the edge portion of the compression plate 40 corresponds to the wall portion 44 and has a different height from the bottom portion 43. Therefore, it is also possible to detect the image of the edge portion from the distance image captured by the TOF camera 39 in the first embodiment. Therefore, instead of the visible light image 90, the distance image captured by the TOF camera 39 may be applied to this embodiment.

Fourth Embodiment

In this embodiment, another aspect in which it is detected whether or not a foreign object is present in the irradiation region 70 of the radiation R using the visible light image 90 captured by the visible light camera 31 will be described. In addition, for a mammography apparatus 10 and a console 12 according to this embodiment, the detailed description of the same configurations and operations as those in the first to third embodiments will not be repeated.

Figure 20:
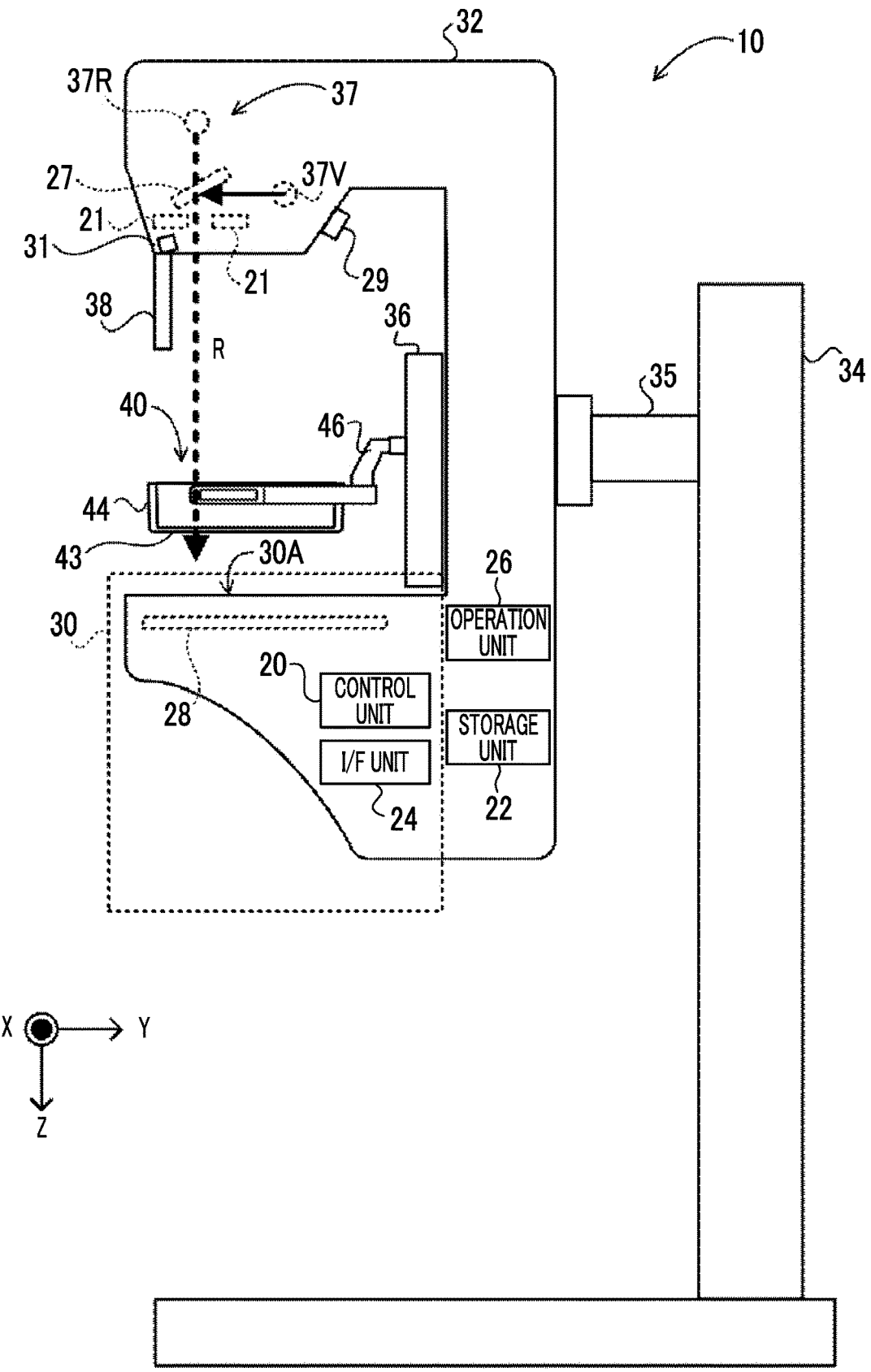
FIG. 20 is a side view illustrating an example of the outward appearance of a mammography apparatus according to a fourth embodiment.
Figure 21:
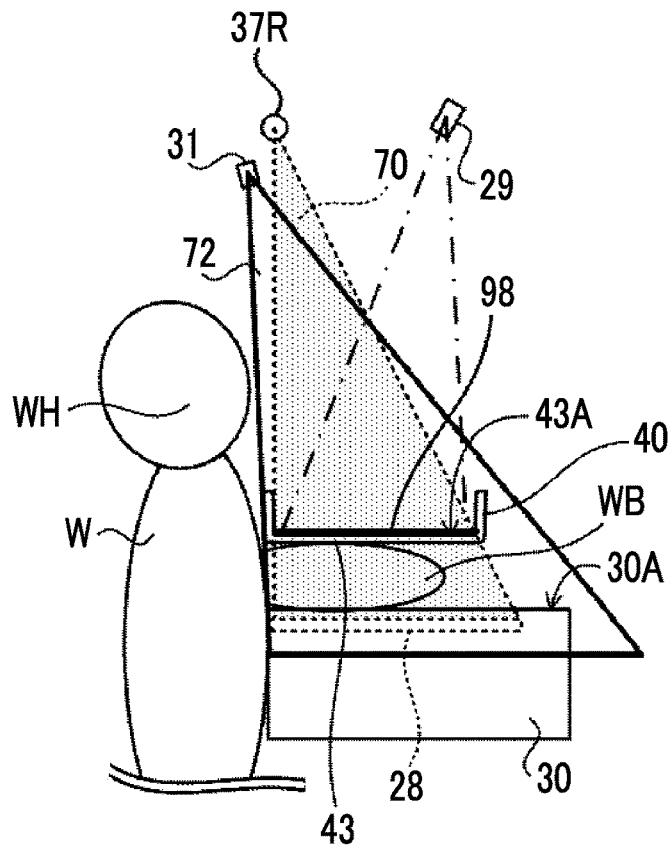
FIG. 21 is a diagram illustrating a projection image projected onto a projection surface.

FIG. 20 is a side view illustrating an example of the outward appearance of the mammography apparatus 10 according to this embodiment. As illustrated in FIG. 20, in the mammography apparatus 10 according to this embodiment, the visible light camera 31 is provided at the same position as that in the mammography apparatus 10 (see FIG. 12) according to the third embodiment. Further, in the mammography apparatus 10 according to this embodiment, a projector 29 is provided at a position of the arm portion 32 that is away from the subject W below the radiation emitting unit 37. As illustrated in FIG. 21, the projector 29 according to this embodiment has a function of projecting a projection image 98 onto an irradiation surface of the compression plate 40 which is irradiated with the radiation R. Specifically, the projector 29 according to this embodiment has a function of projecting the projection image 98 onto a surface (hereinafter, referred to as a projection surface 43A) of the bottom portion 43 of the compression plate 40 which is irradiated with the radiation R. The projector 29 according to this embodiment is an example of an image projection device according to the present disclosure.

In addition, it is preferable that the projection surface 43A of the compression plate 40 is in a state in which the projection image 98 is easily displayed thereon. For example, in a case in which light is incident on the projection surface 43A, most of the light (for example, 90%) may be transmitted, and a portion (for example, 10%) thereof may be specularly reflected by a surface of an object such that an incident angle is equal to a reflection angle. Further, for example, a surface of the bottom portion 43 of the compression plate 40 which faces the radiation source 37R may be roughened to form the projection surface 43A. In addition, for example, a specular reflection sheet may be attached to the surface of the compression plate 40 to form the projection surface 43A. Furthermore, in a case in which the projection surface 43A is a smooth surface such as in a case in which a specular reflection sheet is attached, a surface of the compression plate 40 that comes into contact with the subject W, such as the breast WB, may be the projection surface 43A.

Figure 22:
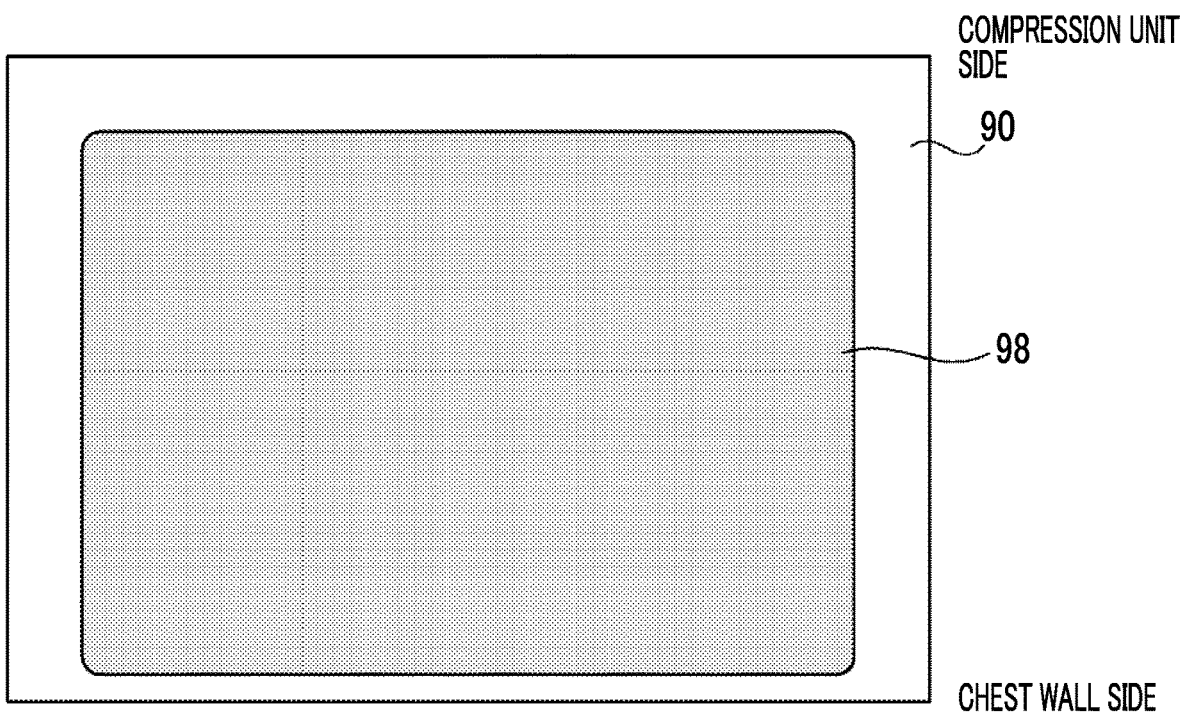
FIG. 22 is a diagram illustrating an example of a visible light image captured by the visible light camera.

FIG. 22 illustrates an example of a visible light image 90 captured by the visible light camera 31 according to this embodiment. As illustrated in FIG. 22, the visible light image 90 captured by the visible light camera 31 includes the projection image 98. In addition, strictly speaking, the visible light image 90 includes an image including the projection image 98 displayed on the projection surface 43A. However, for convenience of explanation, the image including the projection image 98 is also referred to as the projection image 98. The projection image 98 included in the visible light image 90 according to this embodiment is an example of an image of a region corresponding to the inside of an irradiation field of radiation according to the present disclosure.

Figure 23:
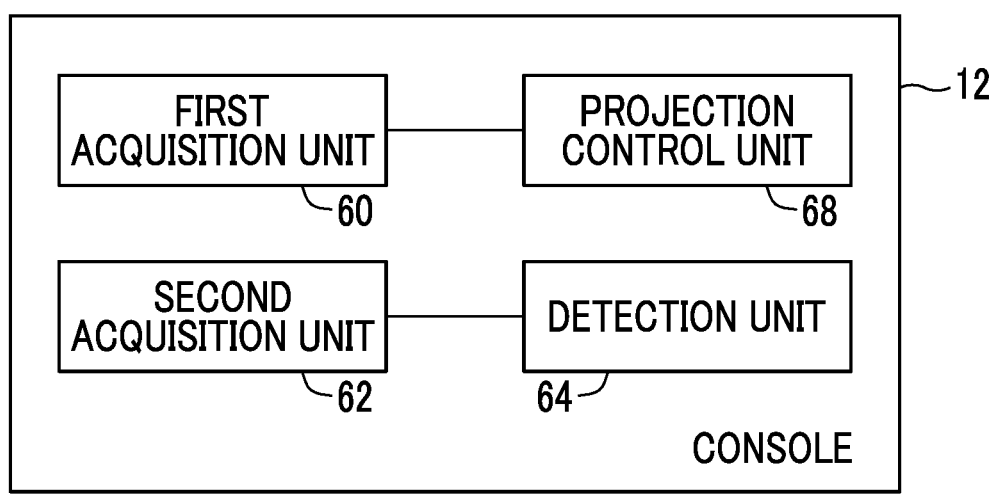
FIG. 23 is a functional block diagram illustrating an example of a functional configuration of a console according to the fourth embodiment.

Since the console 12 according to this embodiment has the same overall configuration (see FIG. 5) as that in each of the above-described embodiments, the description of the overall configuration will not be repeated. Meanwhile, since the functional configuration of the console 12 is different from that in each of the above-described embodiments, the functional configuration will be described. FIG. 23 is a functional block diagram illustrating an example of the functional configuration of the console 12 according to this embodiment. As illustrated in FIG. 23, the console 12 according to this embodiment is different from the console 12 (see FIG. 6 and the like) according to each of the above-described embodiments in that it further comprises a projection control unit 68.

The projection control unit 68 has a function of controlling the projector 29 such that the projection image 98 is projected onto a region including the irradiation field 71 of the radiation R. In addition, for example, in this embodiment, the projection image 98 projected onto the projection surface 43A of the compression plate 40 by the projector 29 has the same position and size as the range of the irradiation field 71 of the radiation R on the projection surface 43A of the compression plate 40. Specifically, as illustrated in FIG. 21, the position and size of the projection image 98 are the same as the cross section of the irradiation region 70 on the projection surface 43A in a case in which the irradiation region 70 is blocked by the bottom portion 43.

Figure 24:
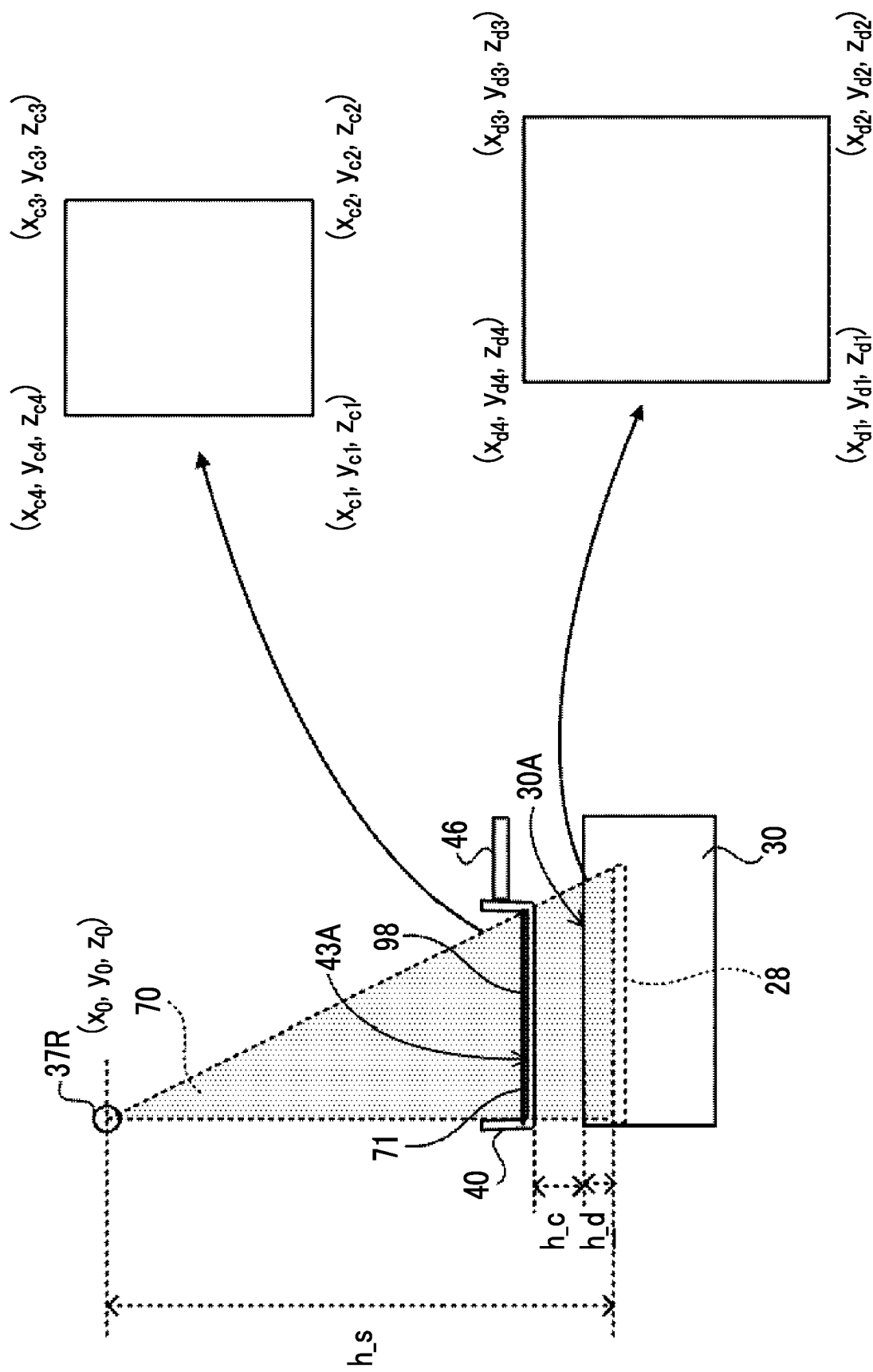
FIG. 24 is a diagram illustrating the position and size of an irradiation field on a projection surface.

Therefore, the projection control unit 68 performs control to make the projection image 98 on the projection surface 43A have the same position and size as the range of the irradiation field 71 of the radiation R on the projection surface 43A (hereinafter, simply referred to as "the range of the irradiation field 71"). As described above, the size and shape of the irradiation field 71 are determined according to, for example, the size of the detection surface (not illustrated) of the radiation detector 28 or the size of the breast WB to be imaged. Therefore, as illustrated in FIG. 24, the size and position of the range of the irradiation field 71 are determined according to the position of the radiation source 37R, a distance h_s between the radiation source 37R and the detection surface of the radiation detector 28 which is a so-called source image distance (SID), a height h_c of the compression plate 40 corresponding to the thickness of the breast WB, and a distance h_d between the imaging surface 30A of the imaging table 30 and the detection surface of the radiation detector 28.

Specifically, assuming that the position of the radiation source 37R is $(x_0, y_0, z_0)$ and the coordinates of four corners of a region irradiated with the radiation R on the detection surface of the radiation detector 28 are $(xd_n, yd_n, zd_n)$ (n=1 to 4), the coordinates $(xc_n, yc_n, zc_n)$ of the projection image 98 on the projection surface 43A can be derived by the following Expression (1).

$$(xc_n, yc_n, zc_n) = (xd_n + (xd_n - x_0))(h\_c + h\_d)/h\_s, (yd_n + (yd_n - y_0))(h\_c + h\_d)/h\_s, (zd_n + (zd_n - z_0))(h\_c + h\_d)/h\_s) \quad (1)$$

In addition, in the above-described Expression (1), the thickness of the bottom portion 43 of the compression plate 40 is ignored. However, more accurately, a value obtained by adding the thickness of the bottom portion 43 to the height h_c of the compression plate 40 is used. Further, in a case in which a specular reflection sheet or the like for displaying the projection image 98 as described above is provided on the projection surface 43A of the bottom portion 43, a value obtained by further adding the thickness of the specular reflection sheet or the like to the compression plate 40 is used.

Therefore, the projection control unit 68 according to this embodiment derives the position and size of the projection image 98 on the projection surface 43A using the above-described Expression (1). In addition, for example, the SID or the coordinates of the radiation source 37R required for using the above-described Expression (1) is included in the information indicating the irradiation region 70 acquired by the first acquisition unit.

The projection control unit 68 controls the projector 29 such that the projection image 98 is projected at the derived position and with the derived size on the projection surface 43A. Specifically, the projection control unit 68 outputs projection image projection information indicating the position and size of the projection image 98 to the projector 29 through the I/F unit 54. The projector 29 projects the projection image 98 on the basis of the projection image projection information input from the console 12. In addition, the method by which the projector 29 projects the projection image 98 on the basis of the projection image projection information is not particularly limited. For example, a projection image 98 corresponding to the size and position of the detection surface of the radiation detector 28 or the imaging surface 30A of the imaging table 30 may be prepared in advance. Then, the prepared projection image 98 may be trimmed on the basis of the projection image projection information to generate projection image data for projecting a desired projection image 98. Further, for example, projection image data of a plurality of projection images 98 corresponding to each of a plurality of assumed positions and sizes may be prepared in advance, and projection image data of a projection image 98 corresponding to the projection image projection information may be selected from the prepared projection image data.

The type of the projection image 98 is not particularly limited. It is preferable that the projection image 98 has a single color, particularly, a single color different from that of the imaging surface 30A of the imaging table 30.

Further, in this embodiment, as described above, the projection image 98 has the same position and size as the range of the irradiation field 71. However, the position and size of the projection image 98 are not particularly limited as long as the projection image 98 includes the range of the irradiation field 71. In addition, in a case in which the size of the projection image 98 is larger than the range of the irradiation field 71, it is preferable that the projection image 98 includes an image indicating the range of the irradiation field 71.

Figure 25:
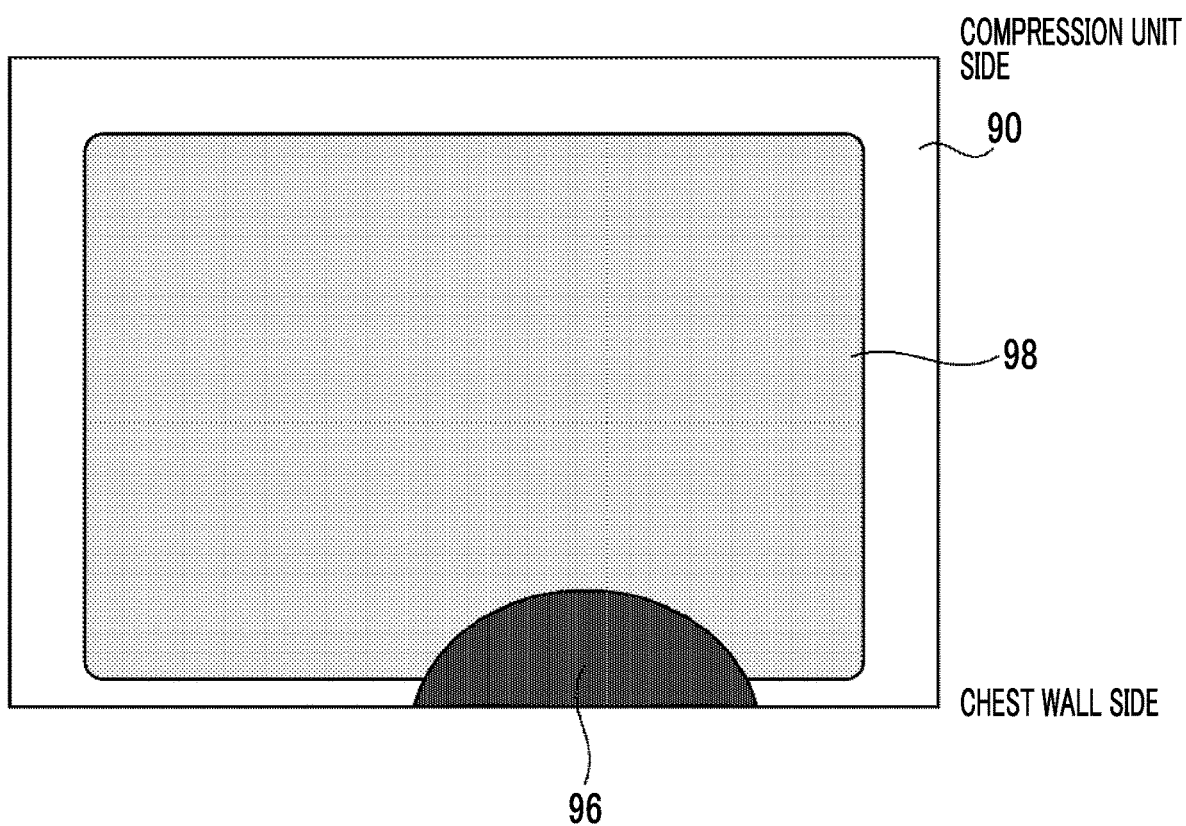
FIG. 25 is a diagram illustrating an example of a visible light image captured by the visible light camera in a case in which a foreign object is present in the irradiation region.

Further, the detection unit 64 according to this embodiment has a function of detecting whether or not a foreign object other than the object to be imaged is present in the irradiation region 70 on the basis of the visible light image 90 acquired by the second acquisition unit. However, the content of the process required for the detection is different. FIG. 25 illustrates an example of a visible light image 90 captured by the visible light camera 31 in a state in which the projection image 98 is projected onto the projection surface 43A and a foreign object enters the irradiation region 70. As illustrated in FIG. 25, a foreign object image 96 appears on the projection image 98 included in the visible light image 90. Therefore, the detection unit 64 according to this embodiment detects whether or not the foreign object image 96 is present on the projection image 98 included in the visible light image 90. In a case in which the foreign object image 96 is present on the projection image 98, it is determined that a foreign object is present in the irradiation region 70. On the other hand, in a case in which the foreign object image 96 is not present on the projection image 98 included in the visible light image 90, the detection unit 64 determines that a foreign object is absent in the irradiation region 70. In addition, in practice, distortion occurs in the visible light image 90 captured by the visible light camera 31 due to a lens of the visible light camera 31. Therefore, it is preferable that the detection unit 64 detects whether or not a foreign object is present in the irradiation region 70, considering the distortion caused by the lens.

Even in a case in which the foreign object image 96 appears on the visible light image 90, a foreign object may not be present in the irradiation region 70. For example, as illustrated in FIG. 25, in a case in which the visible light image 90 is larger than the range of the irradiation field 71, even though the foreign object image 96 appears in a region other than the region corresponding to the range of the irradiation field 71 in the visible light image 90, a foreign object is not present in the irradiation region 70. Therefore, as described above, in this embodiment, the detection unit 64 makes the projection image 98 on the projection surface 43A have the same size as the range of the irradiation field 71 and detects whether or not the foreign object image 96 is present on the projection image 98 included in the visible light image 90, which makes it possible to detect whether or not a foreign object is present in the irradiation region 70 with higher accuracy.

In addition, since the operation of the console 12 according to this embodiment, specifically, the foreign object detection process is different from that in each of the above-described embodiments, the foreign object detection process performed by the console 12 according to this embodiment will be described.

Figure 26:
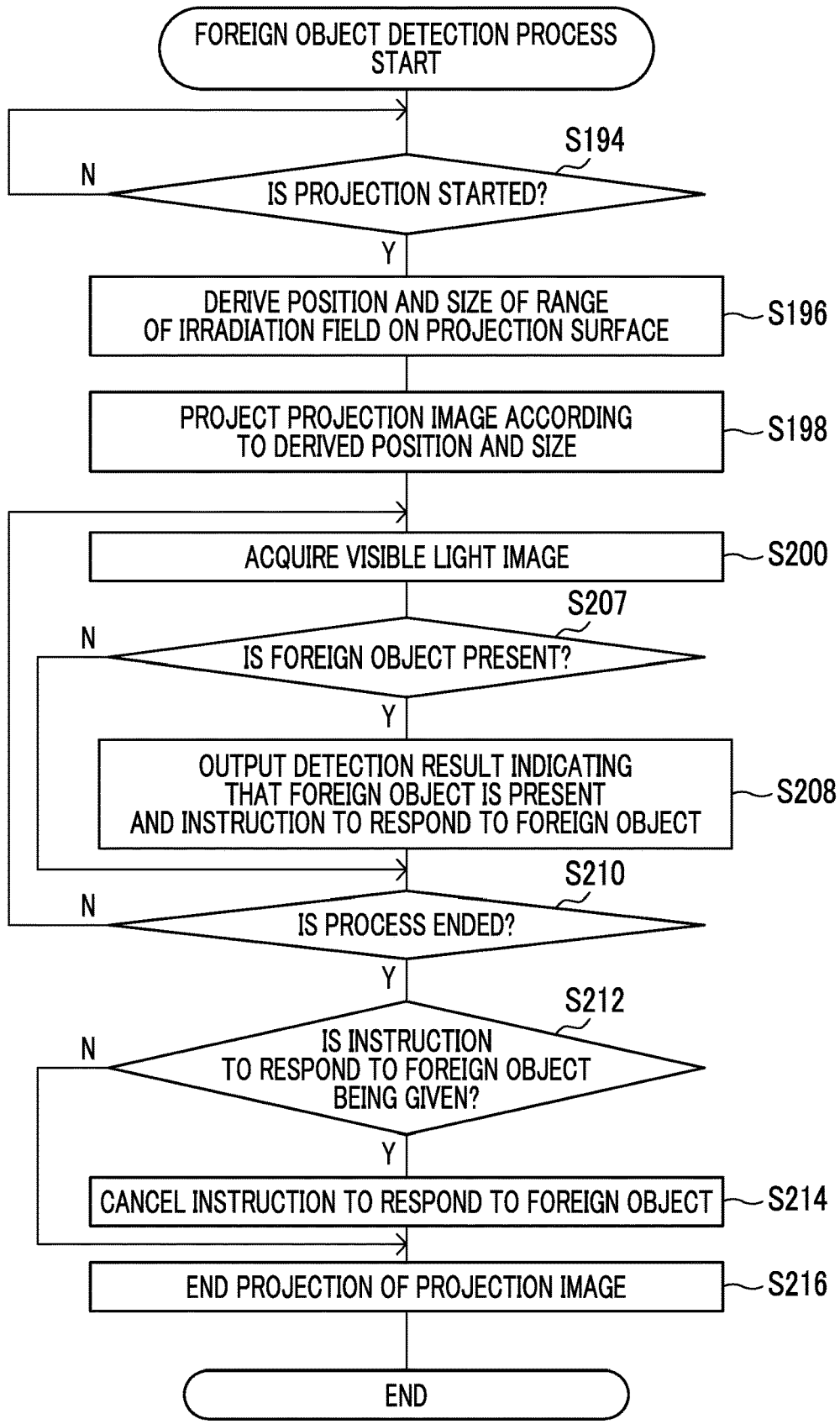
FIG. 26 is a flowchart illustrating an example of the flow of a foreign object detection process of the console according to the fourth embodiment.

FIG. 26 is a flowchart illustrating an example of the flow of the foreign object detection process performed in the console 12 according to this embodiment. The foreign object detection process according to this embodiment illustrated in FIG. 26 is different from the foreign object detection process (see FIG. 17) according to the third embodiment in that it comprises processes in Steps S194 and S196 before Step S200.

As illustrated in FIG. 26, in a case in which the foreign object detection process starts, first, the projection control unit 68 determines whether or not to start the projection of the projection image 98 in Step S194. For example, in this embodiment, the projector 29 starts the projection of the visible light image 90 in a case in which predetermined projection start conditions are satisfied. The projection start conditions are not particularly limited. For example, it is preferable that it is detected whether or not a foreign object is present in the irradiation region 70 after the positioning of the subject W is completed. Therefore, an example of the projection start conditions is a case in which the positioning of the subject W is completed. In this case, the aspect of determining that the positioning of the subject W has been completed is not particularly limited. For example, it is determined that the positioning of the subject W has been completed in a case in which a predetermined time has elapsed since the stop of the movement of the compression plate 40 in a direction in which the breast WB is compressed or since a movement speed was equal to or less than a threshold speed or in a case in which a predetermined time has elapsed since the height of the compression plate 40 was not changed. Further, an example of the projection start conditions is a case in which the user inputs an instruction to start projection using the operation unit 56 or the like.

The determination result in Step S194 is "No" until the projection start conditions are satisfied. On the other hand, in a case in which the projection start conditions are satisfied, the determination result in Step S194 is "Yes", and the process proceeds to Step S196.

In Step S196, the projection control unit 68 derives the position and size of the range of the irradiation field 71 on the projection surface 43A as described above. The projection control unit 68 according to this embodiment derives the coordinates of the projection image 98 on the projection surface 43A which corresponds to the position and size of the range of the irradiation field 71 using the above-described Expression (1).

Then, in Step S198, the projection control unit 68 controls the projector 29 such that the projection image 98 is projected according to the position and size of the range of the irradiation field 71 derived in Step S196 as described above. Further, in some cases, the projector 29 projects an image corresponding to another purpose, in addition to the purpose of detecting a foreign object. For example, in some cases, the projector 29 projects an image or the like, which indicates a skin line of the breast WB in a case in which ideal positioning is performed, onto the projection surface 43A of the compression plate 40 in order to support the positioning of the subject W. As described above, in a case in which the projector 29 projects another image onto the projection surface 43A, the projection control unit 68 performs control to end the projection of other images and to switch to the projection of the projection image 98. Further, the mammography apparatus 10 comprises an irradiation field projection device (see FIG. 27) for displaying the range of the irradiation field 71 with visible light. In a case in which visible light is emitted from the irradiation field projection device to the projection surface 43A, the projection control unit 68 controls the irradiation field projection device such that the emission of the visible light is stopped.

The visible light image 90 acquired by the second acquisition unit 62 in the next Step S200 is changed to the state illustrated in FIG. 22 or the state illustrated in FIG. 25 by the process in Step S198.

Further, as illustrated in FIG. 26, the foreign object detection process according to this embodiment is different from the foreign object detection process (see FIG. 17) according to the third embodiment in that it comprises a process in Step S207 instead of Steps S204 and S206.

In Step S207, the detection unit 64 determines whether or not a foreign object is present in the irradiation region 70. As described above, the detection unit 64 according to this embodiment determines whether or not a foreign object is present in the irradiation region 70 according to whether or not the foreign object image 96 is present on the projection image 98 included in the visible light image 90 acquired in Step S200. In addition, the specific method by which the detection unit 64 determines whether or not the foreign object image 96 is present on the projection image 98 included in the visible light image 90 is not particularly limited. For example, a visible light image 90 (see FIG. 22) captured by the visible light camera 31 in a state in which a foreign object is absent in the irradiation region 70 may be used as a reference projection image, and a projection image included in the reference projection image may be compared with the projection image 98 included in the visible light image 90 acquired in Step S200. In this case, a device that stores the reference projection image is not limited. For example, the reference projection image may be stored in the storage unit 22 of the mammography apparatus 10 or the storage unit 52 of the console 12. Specifically, the detection unit 64 derives a difference between the pixel value of the projection image 98 included in the visible light image 90 and the pixel value of the projection image included in the reference projection image to perform comparison. More specifically, in a case in which there is a region in which a predetermined number or more of pixels in which the absolute value of the difference between the pixel value of the projection image 98 included in the visible light image 90 and the pixel value of the projection image included in the reference projection image is larger than a foreign object detection threshold value are continuous, it is determined that a foreign object is present in the irradiation region 70.

Further, as illustrated in FIG. 26, the foreign object detection process according to this embodiment is different from the foreign object detection process (see FIG. 17) according to the third embodiment in that it comprises a process in Step S216 after Step S214. In Step S216, the projection control unit 68 controls the projector 29 such that the projection of the projection image 98 is ended. In response to this control, the projector 29 ends the projection of the projection image 98. In a case in which the process in Step S216 ends, the foreign object detection process illustrated in FIG. 26 ends.

As described above, the console 12 according to this embodiment directs the projector 29 to project the projection image 98 onto the projection surface 43A of the compression plate 40 and acquires the visible light image 90 obtained by capturing the projection image 98 projected onto the projection surface 43A using the visible light camera 31. The console 12 detects whether or not a foreign object is present in the irradiation region 70 according to whether or not the foreign object image 96 is present on the projection image 98 included in the acquired visible light image 90. Therefore, according to the console 12 of this embodiment, even after positioning is ended by the user or even in a case in which it is difficult for the user to see the irradiation region 70 of the radiation R, it is possible to appropriately detect whether or not a foreign object other than the object to be imaged is present in the irradiation region 70 of the radiation R.

In addition, as illustrated in FIG. 20, the mammography apparatus 10 according to this embodiment comprises a visible light source 37V, and visible light V which has been emitted from the visible light source 37V and reflected by the mirror 27 is projected to indicate the irradiation field 71. In a case in which the projector 29 projects the projection image 98 onto the projection surface 43A of the compression plate 40 and the visible light image 90 obtained by capturing the projection image 98 projected onto the projection surface 43A is acquired by the visible light camera 31, the irradiation by the visible light source 37V is stopped, which makes it possible to more clearly acquire the visible light image 90.

Further, in the above-described embodiment, the aspect in which the visible light image 90 obtained by capturing the projection image 98 projected from the projector 29 is used has been described. However, in a case in which the mammography apparatus 10 comprises an irradiation field projection device that indicates the range of the irradiation field 71 with visible light, the visible light image 90 obtained by capturing the visible light indicating the range of the irradiation field 71 may be used instead of the projection image 98. Specifically, a visible light image 90 obtained by imaging a state in which visible light is emitted to the projection surface 43A by the irradiation field projection device may be used.

Figure 27:
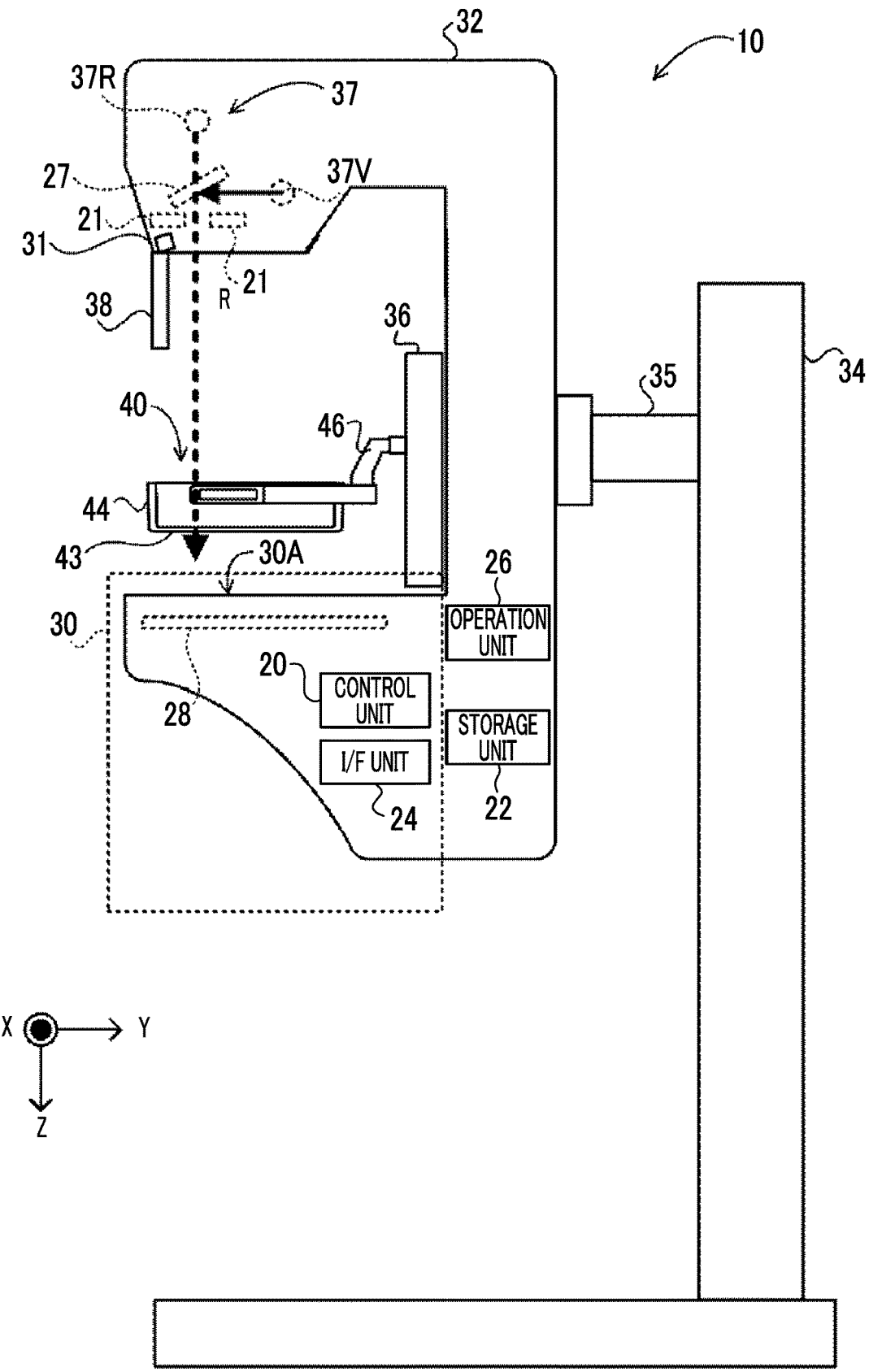
FIG. 27 is a side view illustrating an example of the outward appearance of the mammography apparatus according to the fourth embodiment.

FIG. 27 is a side view illustrating an example of the outward appearance of the mammography apparatus 10 according to this embodiment. As illustrated in FIG. 27, the mammography apparatus 10 according to this embodiment comprises a collimator 21, a mirror 27, and a visible light source 37V instead of the projector 29 of the mammography apparatus 10 (see FIG. 20) according to the above-described embodiment. The collimator 21, the mirror 27, and the visible light source 37V according to this embodiment are an example of an irradiation field projection device according to the present disclosure.

In a case in which a voltage is applied to the visible light source 37V, the visible light source 37V is turned on to generate the visible light V and emits the generated visible light V. For example, in the mammography apparatus 10 according to this embodiment, the visible light source 37V is provided outside the irradiation region 70 of the radiation R.

The mirror 27 reflects the visible light V emitted from the visible light source 37V to the imaging surface 30A of the imaging table 30 such that the irradiation field 71 of the radiation R is indicated by the visible light. The mirror 27 transmits the radiation R emitted from the radiation source 37R.

The collimator 21 has a function of limiting the irradiation field 71 of the radiation R and the visible light. As illustrated in FIG. 27, the collimator 21 is provided between the mirror 27 and the imaging table 30. The irradiation field 71 is limited according to an opening portion of the collimator 21.

In the case of the mammography apparatus 10 illustrated in FIG. 27, the projection control unit 68 of the console 12 may perform control to direct the visible light source 37V to emit visible light corresponding to the range of the irradiation field 71, instead of performing control to direct the projector 29 to project the projection image 98.

Further, the visible light image 90 captured by the visible light camera 31 in a state in which the projection surface 43A is irradiated with the visible light from the visible light source 37V includes an image (hereinafter, referred to as a "light irradiation field image") corresponding to a region irradiated with the visible light in the projection surface 43A, instead of the projection image 98 included in the visible light image 90. Therefore, instead of detecting whether or not the foreign object image 96 is present on the projection image 98 included in the visible light image 90, the detection unit 64 can detect whether or not the foreign object image 96 is present on the light irradiation field image included in the visible light image 90 to detect whether or not a foreign object is present in the irradiation region 70.

As described above, the console 12 according to each of the above-described embodiments comprises the CPU 50A as at least one processor and the ROM 50B storing the commands that can be executed by the CPU 50A. The CPU 50A acquires the distance image or the visible light image captured by the TOF camera 39 or the visible light camera 31 that has an imageable region (72) as a region including the irradiation region 70 which is a space in which the radiation source 37R emits the radiation R to the breast WB of the subject imaged by the mammography apparatus 10 and detects whether or not a foreign object other than the object to be imaged is present in the irradiation region 70 on the basis of the distance image or the visible light image.

As described above, the console 12 according to each of the above-described embodiments can detect whether or not a foreign object is present in the detection region 74 on the basis of the distance image captured by the TOF camera 39 or the visible light image captured by the visible light camera 31. Therefore, according to the console 12 of each of the above-described embodiments, even in a case in which the subject W moves after positioning is completed by the user or even in a case in which it is difficult for the user to see the irradiation region 70 of the radiation R, it is possible to appropriately detect whether or not a foreign object other than the object to be imaged is present in the irradiation region 70 of the radiation R. As a result, according to the console 12 of the above-described embodiments, it is possible to appropriately detect whether or not a foreign object other than the object to be imaged is present in the irradiation region 70 of the radiation R.

Further, according to the console 12 of each of the above-described embodiments, it is possible to appropriately detect whether or not a foreign object other than the object to be imaged is present in the irradiation region 70 of the radiation R. Therefore, it is possible to prevent a foreign object from being included in the radiographic image captured by the mammography apparatus 10. This makes it possible to suppress re-imaging caused by so-called image loss.

In addition, in each of the above-described embodiments, even in a case in which it is detected that a foreign object is present in the irradiation region 70, a radiographic image may be captured. Therefore, in a case in which a radiographic image is captured after it is detected that a foreign object is present in the irradiation region 70, it is preferable that the detection unit 64 of the console 12 further detects whether or not the foreign object is included in the captured radiographic image. In this case, the detection unit 64 may detect the foreign object image included in the radiographic image on the basis of the position of the foreign object image 96 detected from the distance image or the visible light image 90. For example, the detection unit 64 may detect whether or not the foreign object image is included in the radiographic image using computer-aided diagnosis (CAD). Further, in a case in which the foreign object image is included in the radiographic image, it is preferable to perform, for example, a process of warning the user of the fact.

Figure 28:
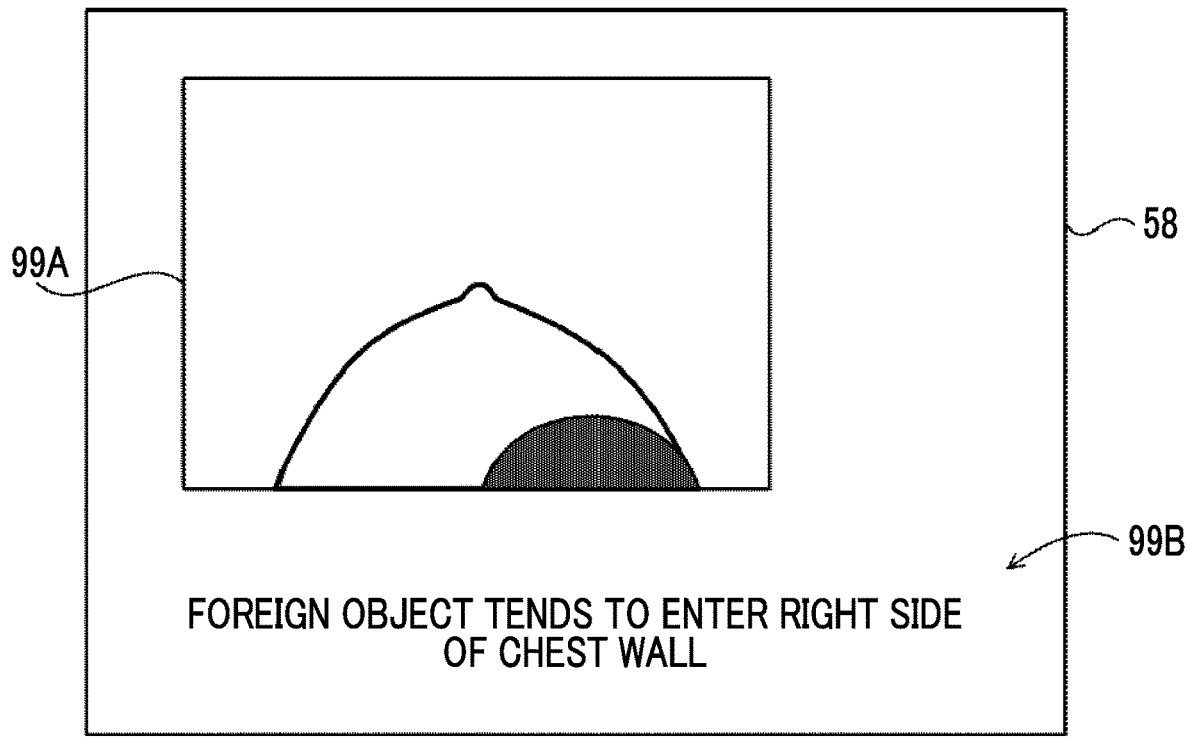
FIG. 28 is a diagram illustrating an example of information for supporting positioning which is displayed on a display unit.

In addition, the detection result of the detection unit 64 showing that a foreign object is present in the irradiation region 70 may be accumulated as foreign object detection result information, and advice or the like may be given to the user who positions the subject W on the basis of the accumulated foreign object detection result information. For example, the position of the foreign object image, the type of imaging, information indicating the user, information indicating the subject W, and the like may be accumulated as the foreign object detection result information to be associated with the visible light image 90 or the distance image including the foreign object image. The accumulated foreign object detection result information is analyzed and a statistical process is performed to extract the condition that a foreign object is likely to enter the irradiation region 70, for example, for each user, each type of imaging, and each condition related to the subject W. Further, the console 12 may display information for supporting positioning by the user on the display unit 58 according to the extracted condition that a foreign object is likely to enter the irradiation region. In this case, FIG. 28 illustrates an example of the information for supporting the positioning which is displayed on the display unit 58. In the example illustrated in FIG. 28, an example is illustrated in which a schematic diagram 99A and advice information 99B that correspond to a typical foreign object corresponding to the extraction result are displayed as the information for supporting the positioning on the display unit 58. The schematic diagram 99A is a diagram obtained by superimposing a foreign object image on a breast schema diagram, a skin line image of the breast WB extracted from a radiographic image, a general breast diagram, or the like. Further, the advice information 99B is information for presenting, to the user, a position or the like where a foreign object tends to be present on the basis of the extraction result. In a case in which the user performs positioning, the information for supporting the positioning which is illustrated in FIG. 28 is displayed on the display unit 58 or the like, which makes it possible to further prevent a foreign object from entering the irradiation region 70.

Figure 29:
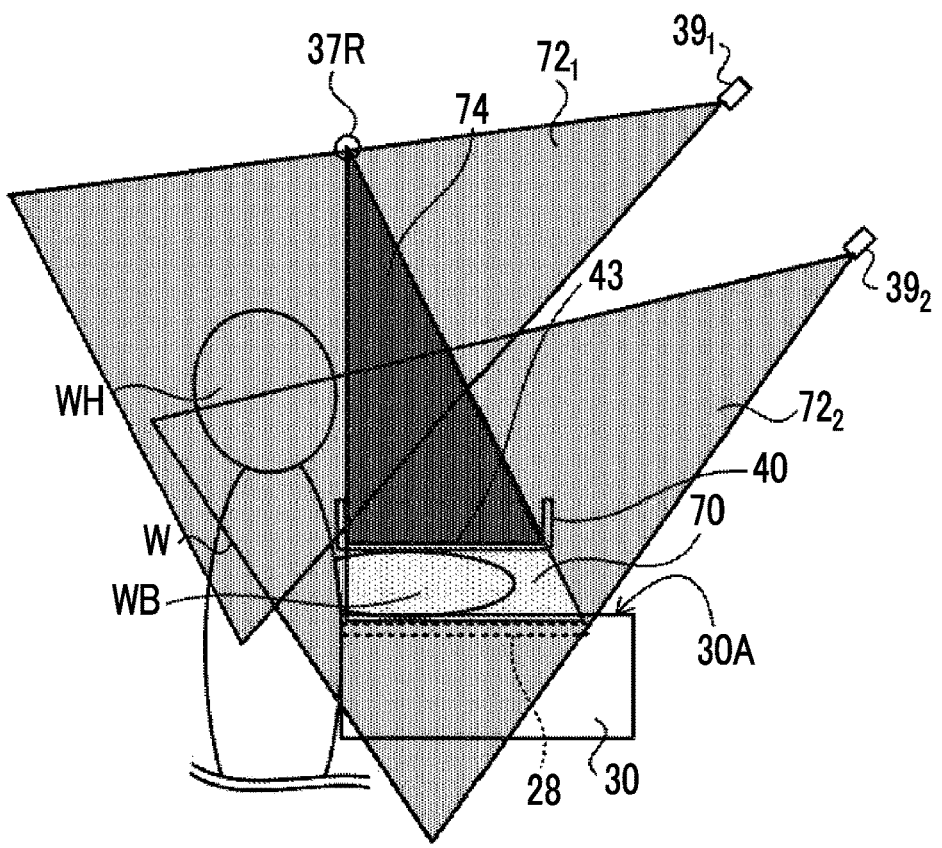
FIG. 29 is a diagram illustrating an aspect in which an irradiation region is included in an imageable region of a plurality of TOF cameras.

In addition, in each of the above-described embodiments, the aspect has been described in which it is detected whether or not a foreign object is present in the irradiation region 70 on the basis of the captured image captured by one imaging device. However, a plurality of imaging devices may be used, and the captured images captured by each of the plurality of imaging devices may be used. For example, as illustrated in FIG. 29, two imaging devices of TOF cameras $39_1$ and $39_2$ may be used. In this case, an imageable region 72 of all of the TOF cameras $39_1$ and $39_2$ which is a combination of an imageable region $72_1$ of the TOF camera $39_1$ and an imageable region $72_2$ of the TOF camera $39_2$ may include the irradiation region 70. Therefore, this configuration is effective for a case in which only one of the imageable region $72_1$ of the TOF camera $39_1$ and the imageable region $72_2$ of the TOF camera $39_2$ is not capable of including the irradiation region 70. In the case of the example illustrated in FIG. 29, for example, a distance image captured by the TOF camera $39_1$ and a distance image captured by the TOF camera $39_2$ are registered and combined into one distance image, which makes it possible to detect whether or not a foreign object is present in the irradiation region 70 as in the first embodiment.

Further, in the first embodiment, the aspect has been described in which the TOF camera 39 is provided on the side close to the compression unit 36 in the radiation emitting unit 37 of the mammography apparatus 10. In the second embodiment, the aspect has been described in which the visible light camera 31 is provided in the vicinity of the collimator 33. However, the position where each of the TOF camera 39 and the visible light camera 31 is provided is not limited to these aspects. Each of the TOF camera 39 and the visible light camera 31 may be disposed in a state in which the irradiation region 70 is included in the imageable region (imageable region 72) as described above, and the positions thereof are not limited. For example, the TOF camera 39 may be provided on the side close to the face guard 38 in the radiation emitting unit 37. Further, for example, the TOF camera 39 or the visible light camera 31 may be provided outside the mammography apparatus 10. Furthermore, for example, in the case where both the TOF camera 39 and the visible light camera 31 are provided, the TOF camera 39 and the visible light camera 31 may be provided side by side at the same position or may be provided at different positions.

Furthermore, in each of the above-described embodiments, the aspect in which the distance image is captured by the TOF method using the TOF camera has been described as an example of the aspect of capturing the distance image. However, the distance image capture device for capturing the distance image is not limited to the TOF camera. For example, the following aspect may be used: a distance image capture device that irradiates an object to be imaged with infrared light having a pattern and captures a distance image corresponding to reflected light from the object to be imaged is used, and a structured light method is applied to capture the distance image. Further, for example, a depth-from-defocus (DFD) method that restores the distance on the basis of the degree of blurring of an edge region in the distance image may be applied. In the case of this aspect, for example, an aspect is known which uses a distance image captured by a monocular camera using a color aperture filter.

Further, in the first and second embodiments, the aspect has been described in which the mammography apparatus 10 is applied as an example of the radiography apparatus according to the present disclosure. However, the radiography apparatus according to the first and second embodiments is not limited to the mammography apparatus. For example, a radiography apparatus for performing general imaging may be applied.

Further, in each of the above-described embodiments, the aspect in which the console 12 is an example of the information processing device according to the present disclosure has been described. However, devices other than the console 12 may have the functions of the information processing device according to the present disclosure. In other words, for example, the mammography apparatus 10 or an external device other than the console 12 may have some or all of the functions of the first acquisition unit 60, the second acquisition unit 62, and the detection unit 64.

In addition, in each of the above-described embodiments, for example, the following various processors can be used as the hardware structure of processing units performing various processes such as the first acquisition unit 60, the second acquisition unit 62, and the detection unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in each of the above-described embodiments, the aspect in which the foreign object detection processing program 51 is stored (installed) in the storage unit 52 in advance has been described. However, the present disclosure is not limited thereto. The foreign object detection processing program 51 may be recorded on a recording medium, such as a compact disc read only memory (CD-ROM), a digital versatile disc read only memory (DVD-ROM), or a universal serial bus (USB) memory, and then provided. In addition, the foreign object detection processing program 51 may be downloaded from an external device through the network.

The disclosure of JP2020-065268 filed Mar. 31, 2020 and JP2020-219603 filed Dec. 28, 2020 are incorporated herein by reference in their entirety.

All of the documents, the patent applications, and the technical standards described in the specification are incorporated by reference herein to the same extent as it is specifically and individually stated that individual documents, patent applications, and technical standards are incorporated by reference.

What is claimed is:

1. An information processing device comprising:
   at least one processor; and
   a memory that stores commands executable by the processor,
   wherein the processor acquires a captured image captured by an imaging device that has, as an imageable region, a region including an irradiation region which is a space in which an object to be imaged by a radiography apparatus is irradiated with radiation emitted from a radiation source and detects whether or not a foreign object other than the object to be imaged is present in a detection region which is a space between the object to be imaged and the radiation source within the irradiation region on the basis of the captured image,
   wherein the radiography apparatus is a mammography apparatus that captures a radiographic image of a breast compressed by a compression member,
   wherein the imaging device is a visible light image capture device that captures, as the captured image, a visible light image obtained by capturing a projection image projected onto an irradiation surface of the compression member, which is irradiated with the radiation, by an image projection device, and
   wherein the projection image projected onto the irradiation surface is projected within a range of an irradiation field of the radiation in a state in which visible light is not emitted by an irradiation field projection device that projects the range of the irradiation field of the radiation with the visible light.

2. The information processing device according to claim 1,
   wherein the radiography apparatus is a mammography apparatus that captures a radiographic image of a breast of a subject, and
   the detection region is a space between a compression member that compresses the breast and the radiation source in the irradiation region.

3. The information processing device according to claim 1,
   wherein the imaging device is a distance image capture device that captures a distance image indicating a distance to the object to be imaged as the captured image.

4. The information processing device according to claim 3,
   wherein the processor detects whether or not the foreign object is present in the detection region using an image corresponding to the detection region in the distance image.

5. The information processing device according to claim 4,
   wherein the processor detects whether or not the foreign object is present in the detection region on the basis of a distance between the imaging device and each position in the detection region derived on the basis of a position of the detection region and a distance between the imaging device and the object to be imaged indicated by the image corresponding to the detection region in the distance image.

6. The information processing device according to claim 3,
   wherein the distance image capture device captures the distance image using a time-of-flight (TOF) method.

7. The information processing device according to claim 1,
   wherein the imaging device is a visible light image capture device that captures a visible light image of the object to be imaged as the captured image.

8. The information processing device according to claim 1,
   wherein the radiography apparatus is a mammography apparatus that captures a radiographic image of a breast compressed by a compression member,
   the imaging device is a visible light image capture device that captures a visible light image of the object to be imaged as the captured image, and
   the processor detects whether or not the foreign object is present on the basis of a chipping of an image of the compression member in the captured image.

9. The information processing device according to claim 8,
   wherein the processor detects whether or not the foreign object is present on the basis of a chipping of a subject on the breast in the image of the compression member.

10. The information processing device according to claim 8,
    wherein the processor uses an image of an edge portion of the compression member as the image of the compression member.

11. The information processing device according to claim 10,
    wherein the processor acquires compression member information indicating a type of the compression member and estimates at least one of a position or a size of the image of the edge portion included in the captured image on the basis of the compression member information.

12. The information processing device according to claim 10,
    wherein the edge portion of the compression member has a color different from a color of at least one of a compression surface, which compresses the breast, in the compression member or an imaging table on which the breast is placed, and
    the processor extracts the image of the edge portion of the compression member from the captured image on the basis of the color of the edge portion.

13. The information processing device according to claim 10,
    wherein the edge portion of the compression member is processed to be distinguishable from an image of a compression surface, which compresses the breast, in the compression member in the captured image, and
    the processor extracts the image of the edge portion from the captured image.

14. The information processing device according to claim 13,
    wherein the edge portion of the compression member is highlighted by at least one of a phosphorescent material or a fluorescent material.

15. The information processing device according to claim 8,
    wherein the processor detects whether or not the foreign object is present on the basis of a chipping of an image of a region corresponding to a type of the imaging in the image of the compression member.

16. The information processing device according to claim 1,
wherein the projection image projected onto the irradiation surface is projected within a range of an irradiation field of the radiation.

17. The information processing device according to claim 1,
wherein the processor detects whether or not the foreign object is present on the basis of an image of a region corresponding to an inside of an irradiation field of the radiation in the captured image.

18. The information processing device according to claim 1,
wherein the processor detects whether or not the foreign object is present on the basis of a comparison result between the projection image and the captured image.

19. The information processing device according to claim 1,
wherein the processor controls the image projection device such that the projection image is projected onto a region including an irradiation field of the radiation.

20. The information processing device according to claim 19,
wherein the processor derives a size and position of the irradiation field on the irradiation surface of the compression member according to a height of the compression member and performs control to project the projection image according to the derived size and position of the irradiation field.

21. The information processing device according to claim 1,
wherein the radiography apparatus is a mammography apparatus that captures a radiographic image of a breast compressed by a compression member, and
the imaging device is a visible light image capture device that captures, as the captured image, an image of a state in which a range of an irradiation field of the radiation is projected onto the compression member by an irradiation field projection device that projects the range of the irradiation field of the radiation with visible light.

22. The information processing device according to claim 1,
wherein, in a case in which it is detected that the foreign object is present, the processor prohibits the emission of the radiation by the radiation source.

23. The information processing device according to claim 1,
wherein, in a case in which it is detected that the foreign object is present, the processor outputs a warning related to the foreign object.

24. The information processing device according to claim 1,
wherein a plurality of the imaging devices are provided, and
an imageable region of all of the plurality of imaging devices, which is a combination of the imageable regions of each of the plurality of imaging devices, includes the irradiation region.

25. A radiography apparatus comprising:
the information processing device according to claim 1; and
the imaging device.

26. An information processing method executed by a computer, the information processing method comprising:
acquiring a captured image captured by an imaging device that has, as an imageable region, a region including an irradiation region which is a space in which an object to be imaged by a radiography apparatus is irradiated with radiation emitted from a radiation source; and
detecting whether or not a foreign object other than the object to be imaged is present in a detection region which is a space between the object to be imaged and the radiation source within the irradiation region on the basis of the captured image,
wherein the radiography apparatus is a mammography apparatus that captures a radiographic image of a breast compressed by a compression member,
wherein the imaging device is a visible light image capture device that captures, as the captured image, a visible light image obtained by capturing a projection image projected onto an irradiation surface of the compression member, which is irradiated with the radiation, by an image projection device, and
wherein the projection image projected onto the irradiation surface is projected within a range of an irradiation field of the radiation in a state in which visible light is not emitted by an irradiation field projection device that projects the range of the irradiation field of the radiation with the visible light.

27. A non-transitory computer-readable storage medium storing an information processing program that causes a computer to execute a process comprising:
acquiring a captured image captured by an imaging device that has, as an imageable region, a region including an irradiation region which is a space in which an object to be imaged by a radiography apparatus is irradiated with radiation emitted from a radiation source; and
detecting whether or not a foreign object other than the object to be imaged is present in a detection region which is a space between the object to be imaged and the radiation source within the irradiation region on the basis of the captured image,
wherein the radiography apparatus is a mammography apparatus that captures a radiographic image of a breast compressed by a compression member,
wherein the imaging device is a visible light image capture device that captures, as the captured image, a visible light image obtained by capturing a projection image projected onto an irradiation surface of the compression member, which is irradiated with the radiation, by an image projection device, and
wherein the projection image projected onto the irradiation surface is projected within a range of an irradiation field of the radiation in a state in which visible light is not emitted by an irradiation field projection device that projects the range of the irradiation field of the radiation with the visible light.

* * * * *